US007082833B2

(12) United States Patent
Heyman et al.

(10) Patent No.: US 7,082,833 B2
(45) Date of Patent: Aug. 1, 2006

(54) METHOD AND APPARATUS FOR DETERMINING AND ASSESSING A CHARACTERISTIC OF A MATERIAL

(75) Inventors: Joseph S. Heyman, Williamsburg, VA (US); John T. Lynch, Williamsburg, VA (US)

(73) Assignee: Luna Innovations, Blacksburg, VA (US)

( * ) Notice: Subject to any disclaimer, the term of this patent is extended or adjusted under 35 U.S.C. 154(b) by 0 days.

(21) Appl. No.: 10/860,636

(22) Filed: Jun. 4, 2004

(65) Prior Publication Data

US 2005/0072236 A1 Apr. 7, 2005

Related U.S. Application Data

(60) Provisional application No. 60/476,218, filed on Jun. 6, 2003.

(51) Int. Cl.
*G01N 19/08* (2006.01)
*G01N 29/07* (2006.01)

(52) U.S. Cl. .............................. 73/598; 73/602; 73/799

(58) Field of Classification Search ................ 73/597, 73/598, 599, 600, 602, 587, 579, 618, 627, 73/628, 629, 778, 799, 801
See application file for complete search history.

(56) References Cited

U.S. PATENT DOCUMENTS

| 4,014,208 | A | * | 3/1977  | Moore et al. ............. 73/629 |
| 4,015,464 | A |   | 4/1977  | Miller et al. |
| 4,062,227 | A |   | 12/1977 | Heyman |
| 4,117,731 | A |   | 10/1978 | Heyman |
| 4,265,120 | A | * | 5/1981  | Morris et al. ............. 73/600 |
| 4,363,242 | A |   | 12/1982 | Heyman |
| 4,413,518 | A | * | 11/1983 | Jones ...................... 73/615 |
| 4,471,657 | A | * | 9/1984  | Voris et al. .............. 73/597 |
| 4,624,142 | A |   | 11/1986 | Heyman |
| 4,823,609 | A | * | 4/1989  | Yost ........................ 73/799 |
| 4,843,346 | A |   | 6/1989  | Heyman et al. |
| 5,115,681 | A | * | 5/1992  | Bouheraoua et al. ...... 73/801 |
| 5,170,366 | A | * | 12/1992 | Passarelli ................. 702/41 |

(Continued)

OTHER PUBLICATIONS

Notification of Transmittal of the International Search Report or the Declaration mailed Dec. 28, 2005 and Written Opinion of the International Searching Authority mailed Dec. 28, 2005 in corresponding PCT Application PCT/US04/17964.

(Continued)

*Primary Examiner*—Hezron Williams
*Assistant Examiner*—Rose M. Miller
(74) *Attorney, Agent, or Firm*—Nixon & Vanderhye P.C.

(57) ABSTRACT

An acoustic energy-based, non-contact or contact testing approach provides low cost, highly accurate, and reliable information to (a) identify flaws and anomalies and (b) assess the integrity of a particular material. This approach is not hindered by surface conditions or impediments, and indeed, looks beneath the surface of the material by propagating an acoustic wave through the material using two differential transducers. A dynamic differential measurement is made of the material under a load condition and an unloaded condition that allows identification and assessment of various characteristics of the material. Multiple "windows" of information may be generated that permit (a) direct detection of flaws, defects, and anomalies using a scattering technique, (b) detection of crack closure and opening used to assess the stability of the material, (c) determination of strain on the material which relates to its performance, and (d) determination of defect dynamics linked to the defect size and stability.

64 Claims, 12 Drawing Sheets

U.S. PATENT DOCUMENTS

| | | | |
|---|---|---|---|
| 5,172,591 A * | 12/1992 | Bohon | 73/152.55 |
| 5,237,516 A | 8/1993 | Heyman | |
| 6,009,759 A * | 1/2000 | Kibblewhite et al. | 73/761 |
| 6,155,292 A * | 12/2000 | Kurata | 137/552 |
| 6,330,827 B1 | 12/2001 | Johnson et al. | |
| 6,543,288 B1 * | 4/2003 | Blouin et al. | 73/643 |
| 2002/0121132 A1 * | 9/2002 | Breed et al. | 73/146 |

OTHER PUBLICATIONS

Heyman et al.; "A Differential Guided Wave Nonlinear Spectroscopy System;" U.S. Appl. No. 60/476,218, filed Jun. 6, 2003.

Heyman et al.; "Bond Testing System, Method, and Apparatus;" U.S. Appl. No. 10/816,667, filed Apr. 2, 2004.

Joseph S. Heyman; "Residual Stress Characterization with a Magnetic/Ultrasonic Technique;" proceedings of IEEE, 1984 Ultrasonics Symposium, Dallas, TX; Nov. 14-16, 1984; pp. 950-954.

Sidney G. Allison, Joseph S. Heyman, and K. Salama; "Ultrasonic Measurement of Residual Deformation Stress in Thin Metal Plates Using Surface Acoustic Waves;" proceedings of IEEE 1983 Symposium, Atlanta, GA; Oct. 31-Nov. 2, 1983; pp. 995-999.

Joseph S. Heyman and Larry L. Yoder; "An Interferometric Measurement of the Acoustoelastic Constant of Rock Core Samples;" proceedings of IEEE, 1983 Symposium, Atlanta, GA; Oct. 31-Nov. 2, 1983; pp. 980-983.

Joseph S. Heyman and Wolfgang Issler; "Ultrasonic Mapping of Internal Stresses;" proceedings of IEEE 1982 Ultrasonics Symposium, San Diego, CA; Oct. 27-29, 1982; pp. 893-897.

Joseph S. Heyman; "A CW Ultrasonic Bolt-Strain Monitor;" SESA Experimental Mechanics, 17; 1977; p. 183.

J.E. Lynch, J.S. Heyman, and A.R. Hargens; "Ultrasonic Device for the Noninvasive Diagnosis of Compartment Syndrome;" Physiological Measurement, vol. 25, Issue 1, 2004; pp. N1-N9.

Robert S. Rogowski, Milford S. Holben, Patrick Sullivan, and Joseph S. Heyman; "A Method for Monitoring Strain in Large Structures: Optical and Radio Frequency Devices;" presented at the Review of Progress in Quantitative Nondestructive Evaluation, Williamsburg, VA; Jun. 21-26, 1987; pp. 559-563.

Sidney G. Allison, Joseph S. Heyman, Min Namkung, and K. Salama; "Ultrasonic Characterization of Plastic Deformation in Metals;" Review of Progress in Quantitative NDE; Plenum Press, New York (1986); pp. 1565-1573.

"Pulsed Phase-Locked-Loop Strain Monitor" A high-resolution, fully-automated strain monitor; NASA Tech Brief; Langley Research Center, Hampton, VA; Spring 1981, B-81-10068, LAR-12772.

S.G. Allison, J. S. Heyman, K. Smith, and K. Salama; "Effect of Prestrain Upon Acoustoelastic Properties of Carbon Steel;" 1984 Ultrasonics Symposium; NASA Langley Research Center, Hampton, VA; pp. 997-1002.

J. Frankel and W. Scholz; "Ultrasonic Studies of Stresses and Plastic Deformation in Steel During Tension and Compression;" US Army Armament Research, Development, & Engineering Ctr., Watervliet, NY; pp. 1577-1584.

J. S. Heyman, S. G. Allison, and K. Salama; "Influence of Carbon Content on Higher-Order Ultrasonic Properties in Steels;" 1983 Ultrasonics Symposium; NASA-Langley Research Center, Hampton, VA; University of Houston, TX; pp. 991-994.

M. Namkung, R. DeNale, and D. Utrata; "Uniaxial Stress and Wave Mode Dependence of Magnetoacoustic Responses in Iron-Base Alloys;" NASA Langley Research Center, Hampton, VA.

* cited by examiner

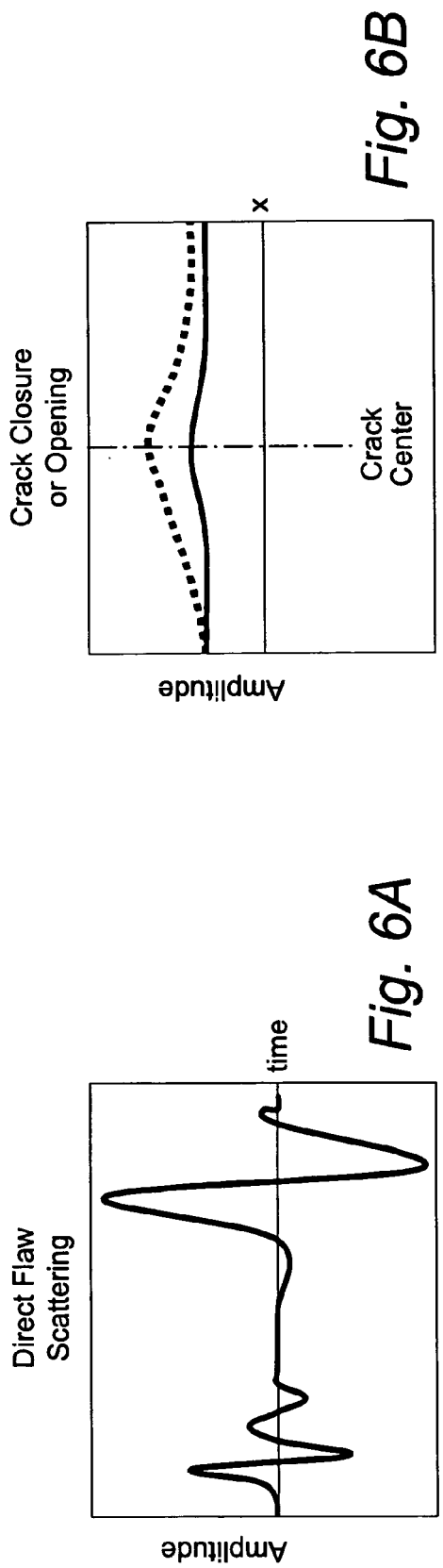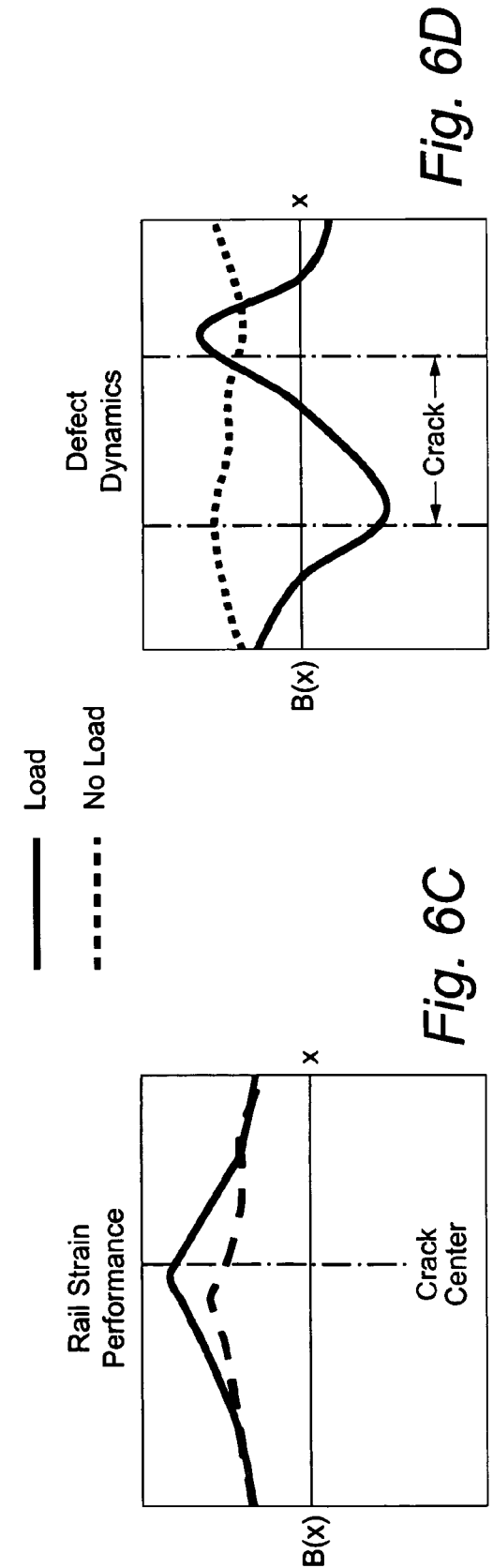

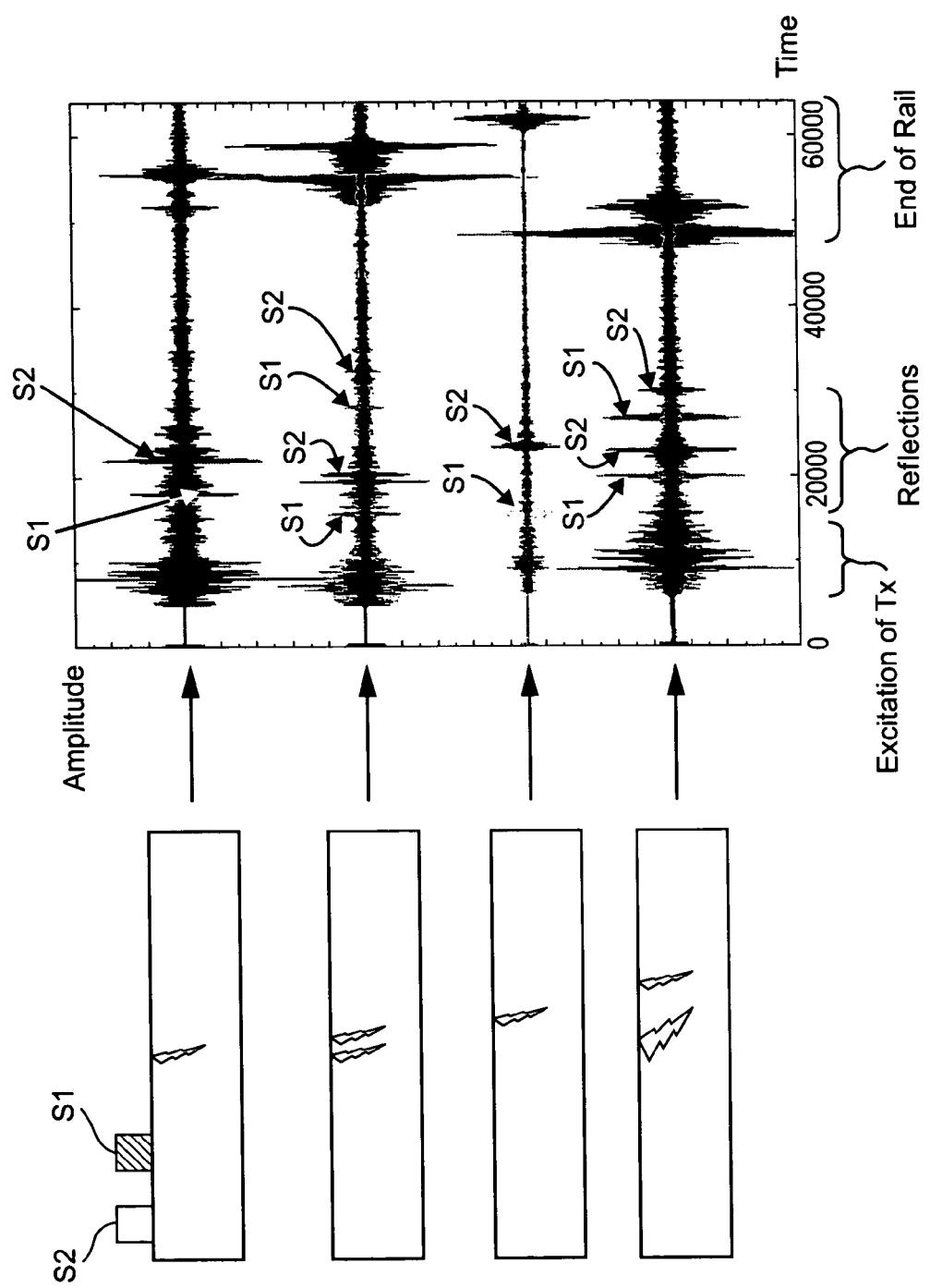

METHOD AND APPARATUS FOR DETERMINING AND ASSESSING A CHARACTERISTIC OF A MATERIAL

CROSS-REFERENCES TO RELATED APPLICATIONS

This application claims domestic priority from provisional application Ser. No. 60/476,218 filed Jun. 6, 2003, the disclosure of which is incorporated herein by reference.

FIELD OF THE INVENTION

The present invention relates to a method and apparatus for determining characteristics of a material. One non-limiting and example application is inspection of rails in a railway system to detect flaws, cracks, or other changes in the rail that may impact the safety or performance of the railway system. There are many other related and unrelated applications.

BACKGROUND

Non-Destructive Evaluation (NDE) equipment is used to detect the presence of certain flaws, such as cracks, in various structures such as rails, airplanes, automobiles, nuclear reactor systems, pipes, etc. While most NDE equipment aims to detect the presence of such cracks, flaws, or anomalies, etc. at the surface of a structure, it is desirable to also detect their presence beneath the structure surface to more reliably identify portions of the structure at risk and to prevent failure of the structure with potentially catastrophic results. Moreover, NDE techniques traditionally identify certain flaws or defects, but do not evaluate or otherwise assess performance effects of identified potential flaws, cracks, or anomalies. Nor do they provide a mechanism for documenting a history and assessing the performance integrity of the material under test over time.

Some current NDE approaches utilize ultrasonic techniques, but these ultrasonic techniques typically require context scanning of the material under test. Ultrasonic NDE techniques generally scan the material with ultrasonic energy and monitor the reflected, scattered, or transmitted sound energy. Other NDE approaches use infrared thermal energy by imaging a sample surface that is flash-heated and the decay of the surface temperature is monitored by an infrared camera. Drawbacks with thermal imaging include the need for flash-heating the test material, often requiring coating the test material, and also the need for expensive and sophisticated thermal imaging and processing equipment. Thermographic techniques are also not particularly effective with respect to detecting deep, subsurface flaws or relatively small surface flaws. Radiographic NDE techniques typically radiate the material using X-rays, but the accuracy of radiographic techniques is generally less than satisfactory for small defects, and the radiation source poses a health/safety risk.

There is also a question about the reliability of ultrasonic, thermal imaging, and radiographic NDE techniques. For example, in the context of a railway application, it must be appreciated that conventional rail inspection in a railway system is based on ultrasonic pulse echo technology using wheel-launched acoustic energy at specific propagation angles to achieve insonification of the rail. Nevertheless, there are thousands of rail incidents per year, some costing millions of dollars. And although these NDE techniques may be workable in a laboratory environment or for small amounts of material to be tested, they are less practical when it comes to testing materials in the field or large quantities of material, e.g., miles of railway tracks, piping, etc. NDE performance may also be adversely effected by dirt, grease, corrosion, chemical reactions, etc. on the surface layer of the material to be tested.

SUMMARY

These and other drawbacks with prior NDE equipment and NDE approaches are overcome with an acoustic energy-based, differential, non-contact (or contact) testing approach that provides low cost, highly accurate, and reliable information to (a) identify flaws and anomalies and (b) assess the integrity of a particular material. This approach is not hindered by surface conditions or impediments, and indeed, looks beneath the surface of the material by propagating and detecting an acoustic wave through the material using differential sensors. A dynamic differential measurement is made of the material under a load condition and an unloaded condition that allows identification and assessment of various characteristics of the material. Multiple "windows" of information may be generated that permit (a) direct detection of flaws, defects, and anomalies using a scattering technique, (b) detection of crack closure and opening used to assess the stability of the material, (c) determination of strain on the material which relates to its performance, and (d) determination of defect dynamics linked to the defect size and stability.

An acoustic wave is first propagated through the material in an unloaded condition. As used herein, "unloaded" includes no load or a lighter load than that in a "loaded" condition. A reflection or a transmission of the acoustic wave is detected, and an acoustic wave parameter is determined therefrom. The same is performed with the material in a loaded condition, and a parameter difference is determined between the parameter for the unloaded condition and that for the loaded condition. From the parameter difference, a characteristic of the material is determined. For example, that characteristic may be a crack, defect, anomaly, microstructure variation, chemistry variation, or flaw in the material. These steps are performed for different positions along the material to generate data corresponding to one or more waveforms representing some characteristic of the material with respect to position. Position can be determined in any suitable fashion. In the example context of a railway testing apparatus, a global positioning system (GPS) may be used to detect position in terms of latitude and longitude.

The characteristic may also be assessed to determine its impact on the integrity of the material. One characteristic assessment example is to determine whether there has been a change in the crack, defect, anomaly, microstructure variation, chemistry variation, or flaw based on the parameter difference. A non-linearity in the waveform data may be used to assess the effect of the crack, defect, anomaly, microstructure variation, chemistry variation, or flaw in the material. The data corresponding to the one or more waveforms may be used to determine one or more of the relationships corresponding to the window (a)–(d) mentioned above.

In one example embodiment, the acoustic parameter corresponds to the transmitted acoustic wave amplitude/velocity or the reflected acoustic wave amplitude/velocity and is determined for different positions along the material in an unloaded condition. Similar amplitudes/velocities are determined for different positions along the material in a loaded condition. The amplitudes/velocities may be formulated as waveform data that may then be analyzed to detect the presence of back-scattering and other patterns (e.g., crack closure or opening) corresponding to a flaw, anomaly, etc. or the progression of same. In an other example embodiment, the determined parameter relates to the acoustic wave velocity that is determined for different positions along the material. The velocities may be formulated as waveform data that may then be analyzed to detect the presence of non-linearities and other patterns that indicate the presence of a flaw, anomaly, etc. or the progression of same. The velocity and amplitude parameter waveform data may be employed alone and/or together to assess the characteristic of the material.

The acoustic wave may be an acoustic surface, guided, shear, compressive, or bulk wave. Preferably, the acoustic wave can propagate under the surface layer of the material and may be, for example, a higher-order, guided-wave such as a Sezawa wave.

Advantageously, these procedures may beperformed without having contact with the material, and in a preferred example embodiment, are implemented using first and second differential sensors separated by a known length. In a non-limiting example application to rail inspection, the first and second sensors are advantageously mounted on a movable load, such as a railway car. One sensor is located near a load bearing point of the car, i.e., over or near a wheel, to sense in a loaded condition, and the other sensor is located away from a wheel to detect an unloaded condition. The differential sensors, in the preferred example embodiment, provide amplitude information and frequency information relating to acoustic waves generated by a transmitter transducer in each differential sensor.

The frequency information of the acoustic waveform generated by the transmitter transducer is provided to phase locking circuitry, and changes in frequency are provided to a controller to determine a velocity parameter of the acoustic wave detected in a receiver transducer in each differential sensor. The controller can also detect a parameter in the environment, such as temperature, and factor that detected parameter into the material characteristic determination. For example, a high environmental temperature may require that the strain or stress determined for the material be reduced by some compensatory amount to prevent buckling or other damage. The controller also preferably stores data in an archive storing the material characteristics at different positions along the material at particular times so that changes of that material characteristic can be monitored over time. Characteristic assessment data may also be transmitted via wireless or other link to appropriate destinations where further assessment and/or remedial action can be taken if necessary.

Where the material characteristic is a crack, acoustic waves are propagated through the material under different load conditions to detect an opening or closing of a crack in the material. In one example embodiment, a waveform is generated related to the detected acoustic wave under different load conditions, and that waveform is analyzed to detect opening or closing of a crack to assess crack stability. The waveform processing may further determine the stress or strain on the material.

BRIEF DESCRIPTION OF THE DRAWINGS

FIGS. 6A–6D illustrate four example "windows" with four different types of waveforms, one or more of which may be used to assess the characteristic of the material;

FIGS. 10A–10D shows four test rails that have different defect conditions and four corresponding graphs showing scattered acoustic waveform evidencing those different conditions;

DETAILED DESCRIPTION

The following description sets forth specific details, such as particular embodiments, procedures, techniques, etc. for purposes of explanation and not limitation. But it will be appreciated by one skilled in the art that other embodiments may be employed apart from these specific details. For example, although the following description is facilitated using a non-limiting example application to rail inspection, the present invention may be employed to inspect and assess any solid, liquid, or gas material in which an acoustic wave can propagate. In some instances, detailed descriptions of well known methods, interfaces, circuits, and device are omitted so as not obscure the description with unnecessary detail. Moreover, individual blocks are shown in some of the figures. Those skilled in the art will appreciate that the functions of those blocks may be implemented using individual hardware circuits, using software programs and data, in conjunction with a suitably programmed digital microprocessor or general purpose computer, using application specific integrated circuitry (ASIC), and/or using one or more digital signal processors (DSPs).

Figure 1:
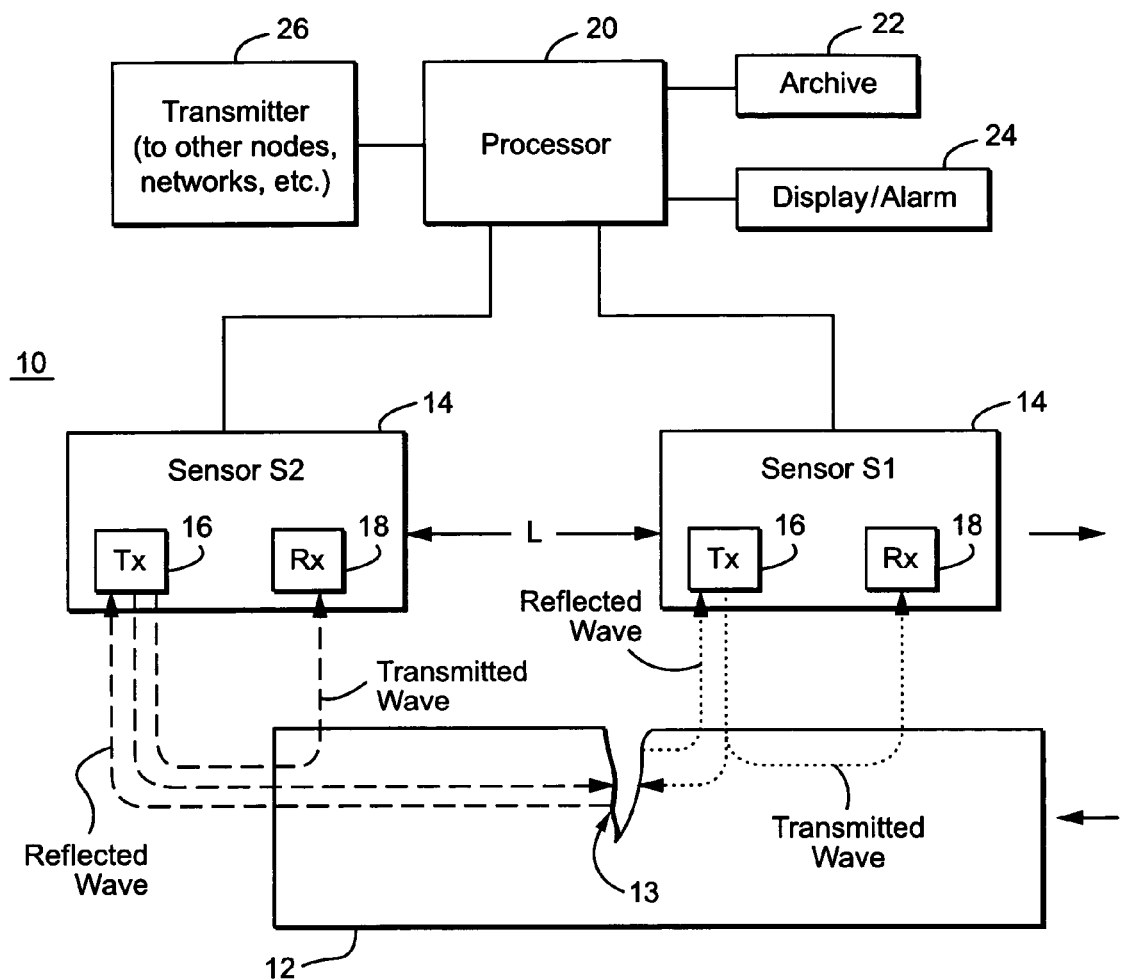
FIG. 1 is a block diagram of a system for detecting and assessing a characteristic of a material.

Reference is made to the material characteristic assessment system 10 shown in FIG. 1. The material 12 to be assessed includes a crack 13. The assessment apparatus includes two sensors 14, denoted sensor S1 and sensor S2, which are separated by length L. Each sensor includes a transmitter (Tx) transducer 16 and a receiver (Rx) transducer 18. The transmitter in sensor S1 generates an acoustic wave that penetrates the surface of the material 12 and traverses along the material 12 in a transmission path and is received through the receiver Rx transducer 18. The transmitted acoustic wave from sensor S1 is also reflected back, and that reflected acoustic wave is detected at the Tx transducer 16 at sensor S1. There is relative movement between the sensors and the material 12, where one or both may be moving.

A processor 20 is coupled to the two sensors S1 and S2 to receive transmitted and reflected acoustic wave information detected by sensor S1 and S2. One of these sensors, in this case sensor S1, provides information to the processor 20 while the material 12 is in an unloaded condition. In contrast, sensor S2 provides information to the processor 20 when the material 12 is under some greater load. For purposes of this application, the term "unloaded" includes no load and a load that is lighter than the load on the loaded sensor. Processor 20 is coupled to an archive 22 which stores characteristic information of the material 12, preferably along with time, date, and location. The processor 20 is also coupled to an optional display and/or optional alarm 24 that may be used to display certain messages, waveforms, etc. generated by the processor 20 related to the characteristics of the material 12. Alarms may be generated if certain characteristics are assessed to be significant, unusual, or potentially unsafe. Processor 20 is also preferably coupled to a transmitter 26 that may be used to transmit certain information to other nodes, networks, operators, etc. through a wireline or wireless link.

Figure 2A:
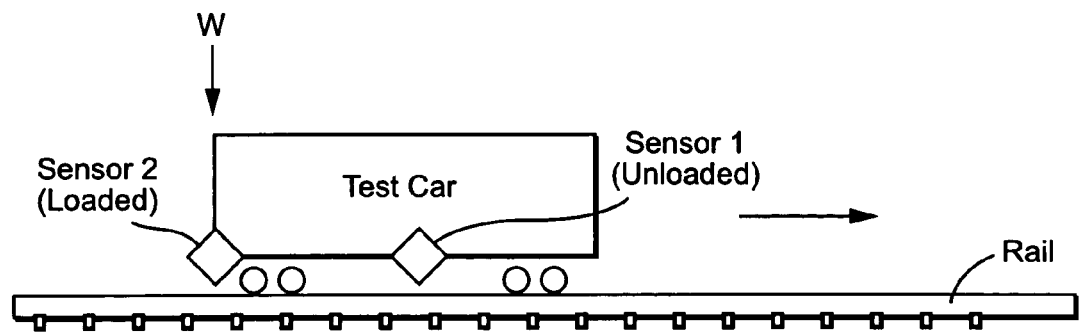
FIG. 2A illustrates a non-limiting example application in which two sensors are located in a test car moving over a railway.
Figure 2B:
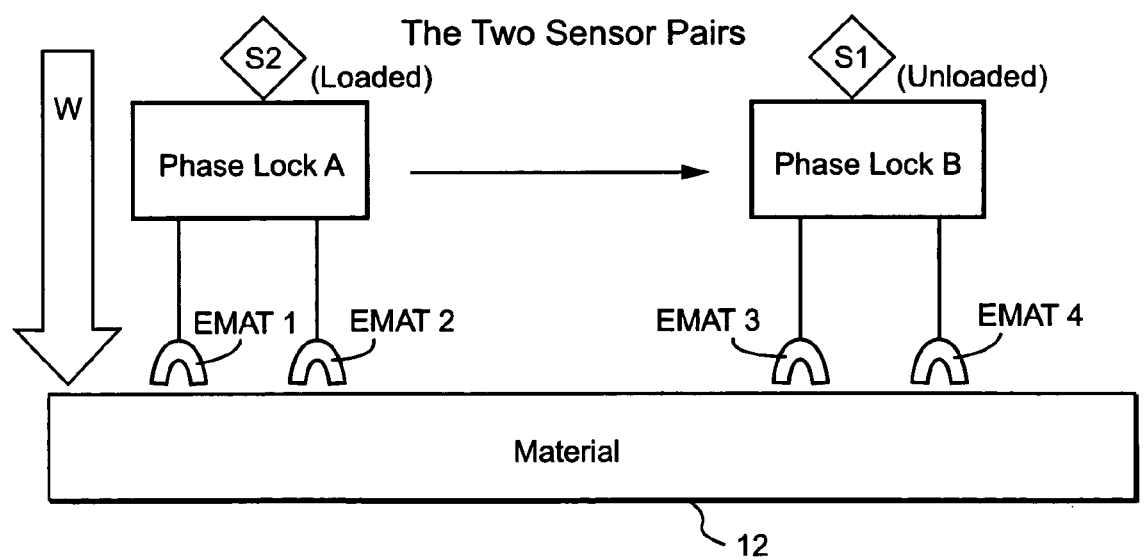
FIG. 2B illustrates that the two test car sensors can be differential in that they including a transmitting acoustic transducer and a receiving acoustic transducer.

In the non-limiting example application to rail inspection, the sensors may be mounted onto a test car as shown in FIG. 2A and the test car moves relative to the fixed rail. Sensor 1 is unloaded because it detects characteristics of the rail as the car moves along the rail at points where the rail is relatively unloaded by the test car, i.e., in between the wheels. In contrast, sensor 2 is located above and close to one of the wheels that transfers the weight, W, of the test car onto the rail. Therefore, sensor 2 is detecting a characteristic of the rail where the rail is under considerably more load than beneath sensor S1.

Advantageously, the sensors do not contact the rail (but they could, if desired). Each sensor, as shown in FIG. 1, is a differential sensor including a transmitter transducer 16 and a receiver transducer 18. FIG. 3B shows that each transducer is preferably, for example, an ElectroMagnetic Acoustic Transducer (EMAT). Other suitable sensors may be employed as well, including, but not limited to piezoelectric and laser ultrasonic wave generation sensors. Each EMAT transmitter transducer may be controlled to generate an acoustic wave over the rail at a particular frequency F1. The acoustic wave may be an acoustic surface, guided, shear, compressive, or bulk wave.

In a preferred, non-limiting embodiment, the acoustic wave is a higher-order, guided wave such as a Sezawa wave. A Sezawa wave is a higher order Rayleigh wave and is desirable because it propagates below the surface of the material. As a result, a Sezawa wave is not affected by surface anomalies including grease, dirt, corrosion, etc. But in order for a Sezawa wave to be generated in the material, such as a rail, a cold-worked layer or a layer of different velocity must exist on top of the material. Test results confirm that typical railroad rails support Sezawa propagation modes and that those modes are relatively unaffected by hard contact, such as a train wheel, on the rail surface.

Figure 3:
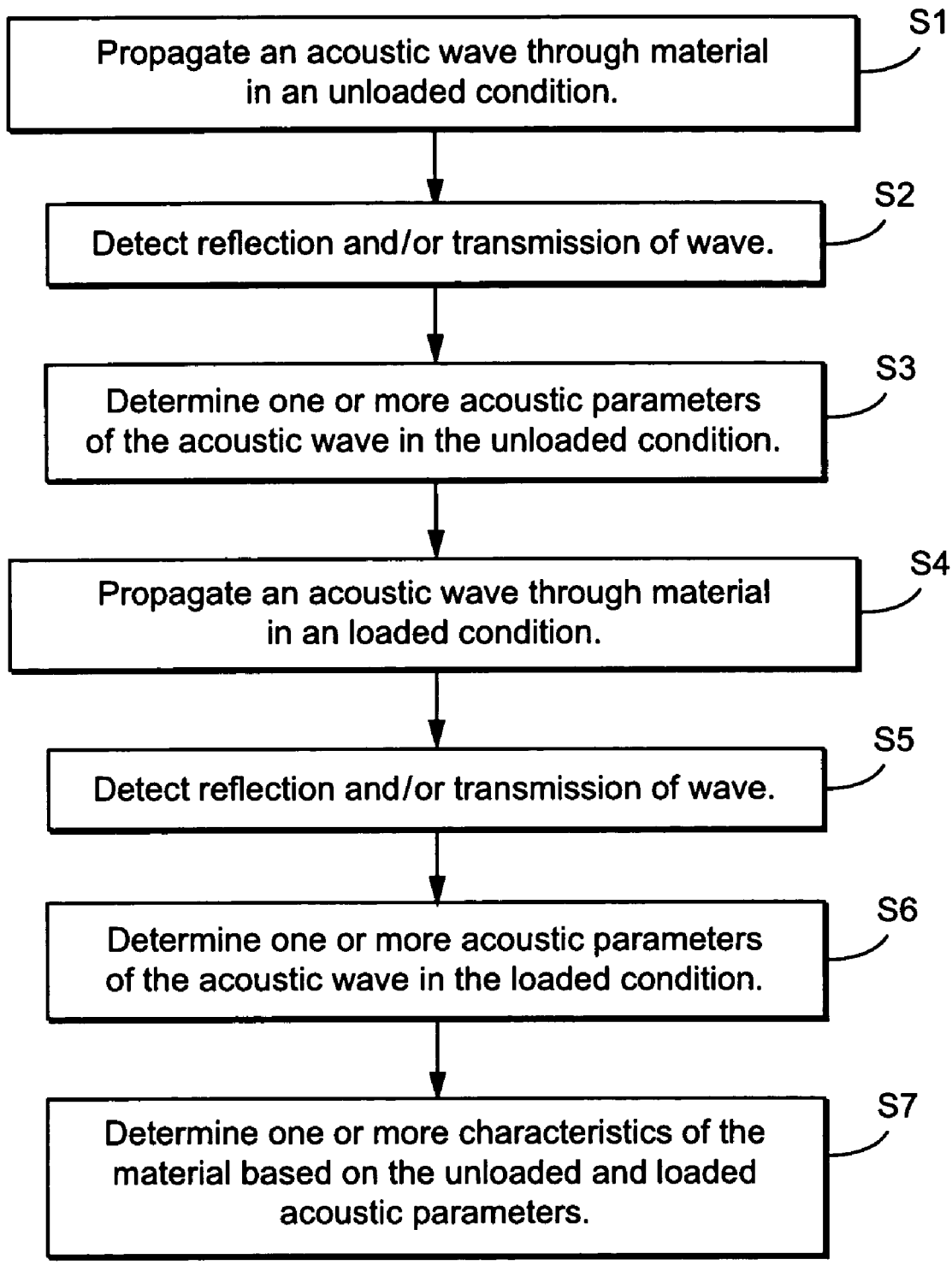
FIG. 3 is a flow chart diagram illustrating non-limiting, example procedures that may be used to detect and assess the characteristic of the material.

FIG. 3 illustrates by example, non-limiting procedures for detecting and assessing a characteristic of a material. First, an acoustic wave is propagated through the material in an unloaded condition (step S1). As shown in FIG. 1, each of the transmitter transducers 16 in both sensors S1 and S2, is capable of propagating an acoustic wave. In this example, sensor S1 is the unloaded sensor and so step S1 pertains sensor S1. A reflection and/or transmission of the acoustic wave is detected (step S2). In the example of FIG. 1, the reflection is detected by the transmitter transducer 16. The transmission is detected by the receiver 18. One or more acoustic parameters of the acoustic wave is determined for the unloaded condition (step S3), e.g., by processor 20 in FIG. 1. Similar steps S4, S5 and S6 are performed under a loaded condition with sensor S2 using its transmitter transducer 16 and receiver transducer 18. Based on the unloaded and loaded acoustic parameters determined in steps S3 and S6, the processor 20 determines one or more characteristics of the material itself (step S7). In addition to the characteristic of the material being possibly a crack, defect, anomaly, or flaw, the characteristic can also be related to a quality of the material, such as the strain or stiffness of the material. Example, non-limiting techniques and apparatus for performing steps S1–S7 are described below.

Figure 4:
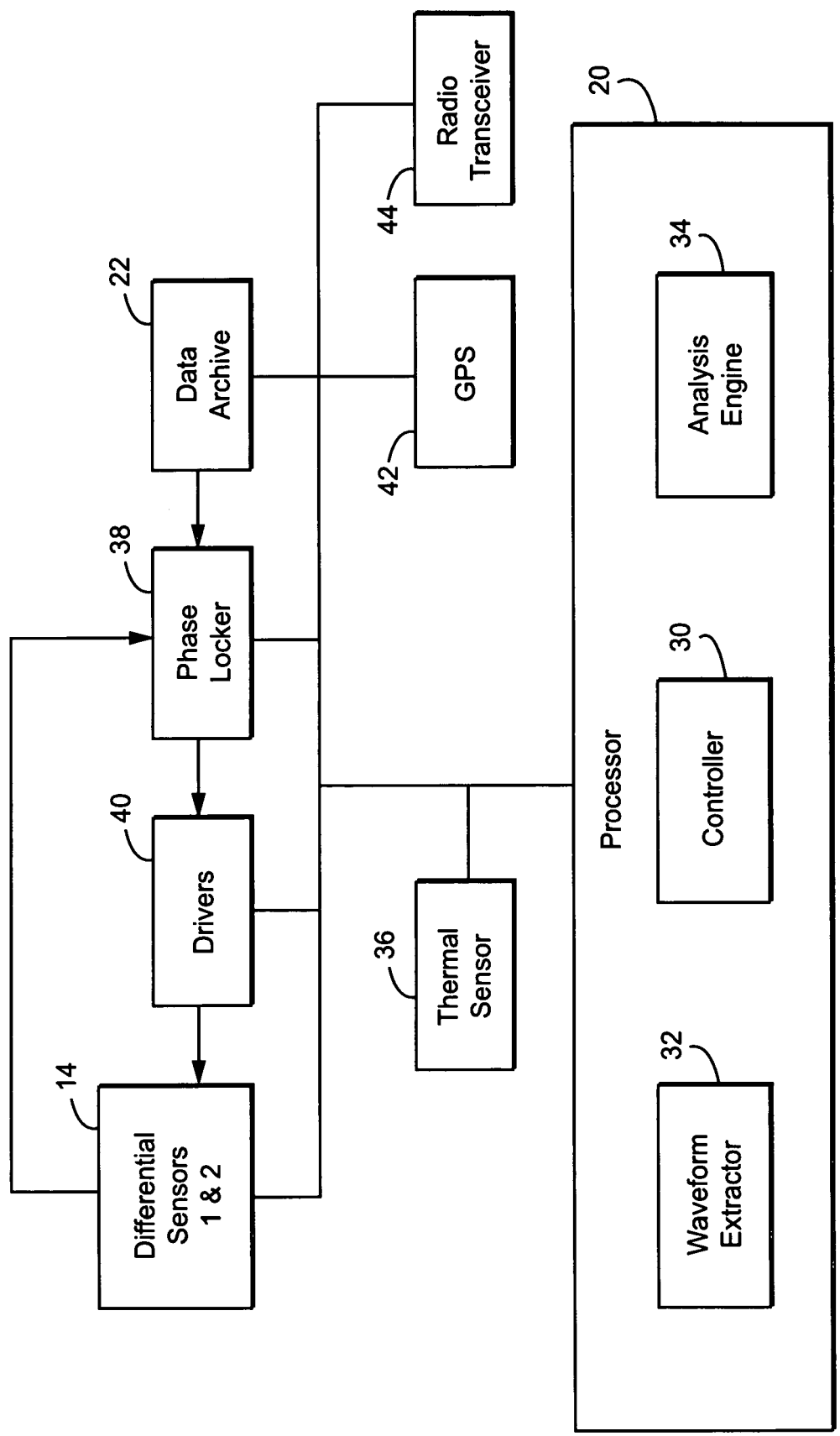
FIG. 4 is a function block diagram of a non-limiting, example apparatus for detecting a characteristic of a material.

FIG. 4 illustrates an example assessment apparatus in which the processor 20 includes a controller 30, a waveform extractor 32, and analysis engine 34. The processor 20 is coupled by a common bus to a number of function blocks including a thermal sensor 36 which is used to detect the temperature of the material. The detected temperature may be used to compensate characteristic assessment calculations sensitive to temperature, e.g., stress, strain, etc. Other environmental parameters may also be taken into account including, for example, humidity, pressure, etc. Also coupled to the processor 20 via the common bus is a data archive 22 which stores data from the differential sensors 14, the processor 20, the thermal sensor 36, and any other sensors, and the global positioning system (GPS) 42, which provides a location in terms of latitude and longitude and date/time for the assessment data. A radio transceiver 44 is coupled to the processor 20 and may be used to communicate data relating to material characteristics and assessments to another node, a network, or other management entity. Processor 20 is coupled to a phase lock loop that includes a phase locker 38, drivers 40, and differential sensor S1 and S2 14 with a detected frequency (from the receiver transducers) feedback to complete the phase lock loop. The phase lock loop is used to measure changes in strain or stress in material 12.

Figure 5:
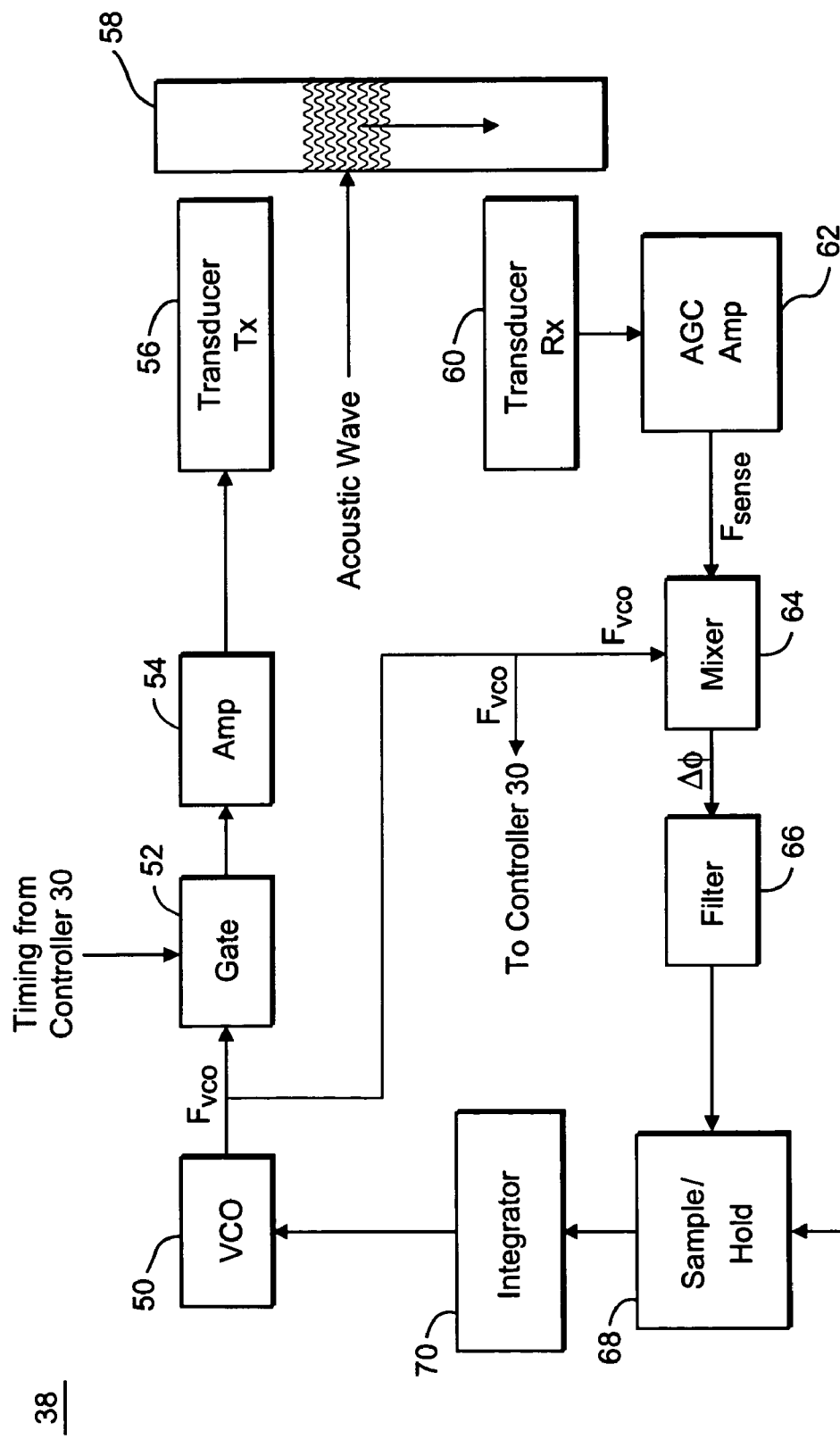
FIG. 5 is the function block diagram illustrating an example implementation of a phase locker shown in FIG. 4.

One non-limiting, example phase locking approach is now described in conjunction with FIG. 5, which shows details of a non-limiting, example phase locker 38. Reference may also be made to U.S. Pat. No. 4,363,242. It should be understood that the phase locker circuitry shown in FIG. 5 is for one sensor and that similar circuitry is provided for each of the two sensors.

FIG. 5 shows a voltage controlled oscillator (VCO) 50 whose radio frequency output $F_{vco}$ is coupled to a gate 50, the timing of which is controlled by controller 30. The VCO output $F_{vco}$ is also provided to the controller 30 and is used to calculate the change in strain or stress of the material 58 as will be explained in further detail below. The VCO frequency output $F_{vco}$ is also supplied to mixer 64.

The gate 52 outputs a signal which is amplified in an amplifier 54 and the transmitter transducer 56 generates an acoustic wave corresponding to that signal which propagates along material 58 as shown to the receiver transducer 60. The receiver transducer 60 detects the acoustic wave having propagated through the material 58. The receiver transducer 60 output is amplified at an automatic gain controller (AGC) amplifier 62, which keeps the level of the detected signal within the dynamic range of the mixer 64.

The acoustic wave has been delayed in the process of propagating through material 58 so that at the initial unlocked frequency, the detected signal $F_{sense}$ is out of the phase relationship that it should have with the frequency $F_{vco}$ output by the VCO. At the quadrature condition, the phase difference is 90° between the reference VCO signal and the measured signal. At quadrature, the voltage output of the mixer 64 is exactly zero. The mixer output voltage is composed of two frequencies: the difference frequency and the sum frequency derived from the two mixer inputs. Since for this example circuit, both inputs come from the VCO, they are at the same frequency, slightly time-shifted by the electronic and acoustic path. The difference frequency, which is at zero Hertz (D.C.), provides the control voltage used in this device. The sum frequency, which is twice the VCO frequency, is removed by the filter 66. In this configuration, the mixer 64 detects a delta Δ phase amount, either lagging or leading, and generates a positive voltage or a negative voltage corresponding to the size and direction of the delta. That voltage is sampled in the sample-and-hold block 68 under the control of timing from controller 30. The sampled output is integrated at integrator 70, the ramp output thereof either increasing or decreasing the output frequency of the VCO 50 in order to reduce the phase difference delta Δ to zero, or "quadrature lock."

The controller 20 detects a change or difference in velocity of the acoustic signal between the loaded and unloaded conditions. The velocity of the acoustic wave moving through material 58 is related to the frequency of that wave by the following relationship:

$$V=2FL/M, \quad (1)$$

where V is the acoustic wave velocity, F is the acoustic wave frequency, L is the effective distance between transmitter and receiver in a given sensor, and M is a constant depending on the wave harmonic. This condition is created with the phase-locking system. Any relative change in the material velocity under test by, for example, moving the sensor S1 along the sample, will be revealed by changes in the frequency, F. If the change in velocity between the transmitter and receiver in S1 as a function of position depends on load, then S2 will produce data permitting the system to identify that situation. If the change is caused by temperature alone, both S1 and S2 will see the same data.

In the context of FIG. 4, the controller 30 receives for each of the sensors S1 and S2 a frequency F1 from the phase locker 38 when the material is an unloaded condition and a frequency F2 when the material is a loaded condition. A normalized frequency difference ΔF/F is then determined for each of the sensors S1 and S2 by subtracting F1 and F2 and dividing the difference by F1. The difference in load ΔL is the difference between the unloaded force and loaded force on the material. Thus, by detecting the change in frequency, we have a measure of the change in wave velocity which is related to a change in stress state or strain in the material. This relationship is simply stated as:

$$[(F2-F1)/F1]*K=\Delta S \quad (2)$$

where S is the material stress or strain and K is a calibration constant. Similarly, the controller 20 also detects a normalized change in amplitude, ΔA, of the acoustic signal between the loaded and unloaded conditions. The normalized change in amplitude is determined in a similar way using:

$$\Delta A=(A2-A1)/A1 \quad (3)$$

A1 is the amplitude of the first loaded measurement, and A2 is the amplitude of the second unloaded measurement.

Using this loaded/unloaded differential measurement of frequency and/or amplitude, the processor 20 can determine one or more parameters of the material being tested. For example, the following equation links the change in frequency per change in load to a non-linear parameter B:

$$(\Delta F/F)/\Delta load=B(x), \quad (4)$$

where x indicates location of position along the material as determined, for example, by a GPS system.

Returning to FIG. 4, the waveform extractor 32 calculates, from the information received from the differential sensors 14 and the phase locker 38, the shape of the measured parameter as a function of x. For example, B(x) is a measure of the nonlinearity parameter B (Eq. 4) as a function of position, x, along the material, such as a rail. Unlike conventional NDE systems, the "map" of B(x) permits the system to assess rail conditions based on the shape of B(x). The waveform extractor 32 calculates similar waveshape information for ΔA as a function of position x from sensors S1 and S2 in the loaded and unloaded conditions. Since ΔA depends on the microstructure shape of the asperity points of contact of a closed crack convolved with the loading geometry, the exact relationship between ΔA and crack behavior is complex. Notwithstanding that complexity, it is true that as the load increases compressing the crack, the transmitted acoustic amplitude will generally increase. Asperity slippage from non-normal loads can reverse this trend, but only over a small range of increasing loads. At some point, plastic deformation will fill most of the asperity points.

The controller 30 samples and stores calculated parameter data B(x) and related A(x) terms in the data archive 22 for historical comparison and other analyses. The controller 30 generates timing control pulses to perform measurement functions including monitoring the thermal sensor output 36, GPS latitude/longitude location, and date/time, controlling the phase locker timings, and obtaining the loaded and unloaded frequencies F2 and F1. The controller 30 also preferably flags critical findings in the data and alerts necessary personnel via radio transceiver 44 or other means. The controller 30 also compensates for temperature-related effects on strain or stress in the material that are superimposed on top of the load condition on the material. For example, the change in detected frequency may be corrected for higher temperatures and/or other environmental factors.

The analysis engine 34 determines the wave shape of the change in frequency over the load as a function of distance, which data is received from the waveform extractor 32. The analysis engine 34 also pre-stores various wave shape patterns formed under conditions of interest with respect to the material characteristic(s) being tested or considered. The analysis engine 34 performs a waveform analysis between the pre-stored waveform shapes and the waveform shapes provided by the waveform extractor 32 related to the material under test. At the simplest level, that analysis may be a simple comparison, but of course, more sophisticated analyses may be performed. A comparison can be done in the time domain, or it may be performed in the frequency domain by taking the Fourier transform of the wave shape, extracting the frequency components, and comparing them. In addition, wave shape parameters may be extracted such as the wave maximum, minimum, and number of slope sign (+,−) changes per unit distance, and distance separation between maximum and minimum values. These parameters are then compared with similar, archived values.

In a preferred, but non-limiting embodiment, the analysis engine 34 generates data corresponding to multiple windows, graphs or relationships relating to the characteristic of the material. For these descriptions, the term "window" is adopted. FIGS. 6A–6D illustrate four example windows that may be generated from the data provided by the analysis engine 34.

FIG. 6A illustrates a direct flaw scattering window plotting an amplitude, A, of an acoustic wave against wave propagation time. As can be seen in FIG. 6A, the first oscillation on the left side of the window corresponds to the generated wave from the transmitter transducer, and the second larger oscillation shown on the right side of the window corresponds to the amplified acoustic wave reflected back to the transmitter transducer, after being back-scattered from a flaw or crack in the material. The analysis engine determines whether this reflected, back-scattered, normalized wave amplitude exceeds a specified normalized amplitude. If so, an alarm or other notification message may be generated.

At the same time, e.g., with the same timing pulse, the analysis engine 34 preferably determines if the transmitted wave normalized amplitude measured by the receiving transducer (as opposed to the transmitting transducer) is lower in amplitude than expected. This lower-than-expected, normalized amplitude at the receiver transducer is caused by back-scattering energy. If both of these conditions exist at the same location in the material at the same time, the analysis engine 34 determines that a scattering flaw exists at that location in the material and that the size of the flaw is related to the reflected normalized amplitude received at the transmitter transducer and the decrease in normalized amplitude received at the receiver transducer. In FIG. 6A, the amplitude of the reflected wave is related to the amplitude of the initial, pulse-generated wave transmitted by the transmitter transducer in each sensor S1 and S2, the distance between the transmitter transducer and the scattering flaw, and the size and geometry of the flaw. The transmitted wave amplitude is related to the amplitude of the initial pulse-generated wave, the distance between the transmitter transducer and the scattering flaw, the distance between the transmitter and receiver transducers in each sensor S1 and S2, and the size and geometry of the flaw. As the flaw size increases, the reflected wave amplitude will increase, and the transmitted wave amplitude will decrease.

FIG. 6B illustrates a crack closure or a crack opening window. For the transmitted wave, if the applied load further opens a closed crack, the amplitude of the transmitted wave will decrease as more energy is scattered by the crack opening geometry. Inversely, if the load causes the crack to further close, more energy will be transmitted, increasing the amplitude of the transmitted wave. As shown in this FIG. 6B, the loaded amplitude is lower in the center of the window corresponding to the crack location. The amplitude of the unloaded waveform at the same crack location peaks up to a higher amplitude. As the material becomes loaded, e.g., the test car wheel presses down on the rail so that the surface of the material is placed in compression causing the crack to close. Here, the amplitude of the transmitted wave between the transmitter transducer and the receiver transducer in each sensor is measured. If the crack is closing (opening) during the loading, the amplitude of the transmitted wave will increase (decrease). The amplitude as a function of distance may also be determined for any reflected wave, i.e., sent from the transmitter transducer and the reflection is received by the transmitter transducer. If the reflected amplitude increases (decreases), a crack is opening (closing).

FIG. 6A is representative of a stable crack utilizing the amplitude of either the loaded or unloaded acoustic wave at a given position, and FIG. 6B utilizes the amplitude of both the unloaded and the loaded acoustic wave in a differential mode as a function of position. Rather than acoustic wave amplitude, FIGS. 6C and 6D focus on acoustic wave velocity. For example, the window in FIG. 6C, labeled as the Rail Strain Performance Window, determines the non-linear function $B(x)=[(F2-F1)/F]/\Delta load$ as a function of distance. As described above, a change in the non-linear function, corresponding to a change in frequency caused by a characteristic of the material being examined, corresponds to a change in strain or stress. The shape of the $B(x)$ wave provides information that permits assessment of crack behavior.

The phase-locking measurement is very sensitive to changes in phase. The acoustic wave phase is shifted by either changes in velocity or path length. Even though the transmitter and receiver transducers in each sensor S1 and S2 are a fixed distance apart, the effective acoustic path length is altered if the wave has to propagate around a crack or through a boundary with asperity points of contact. As the contact points are altered by the applied load, the effective path length decreases for crack closure and increases for crack opening loads. The resulting shape of $B(x)$ is a "map" of the time and load dependant dynamics of the rail. If the cracks are dynamic or changing/changeable, the shape of $B(x)$ indicates the type of flaw.

The shape of the $B(x)$ or strain wave may also be used to determine material support behavior, in other words, how well the material is supported under load, as determined by the support geometry. For example in a railway context, railroad ties upon which the rail is laid are supports. As can be seen in FIG. 6C, the unloaded rail strain is lower at the flaw location as compared to the loaded strain of the rail at the flaw location.

The window in FIG. 6D illustrates defect dynamics in the sense that the waveform can be analyzed by analysis engine 34 to determine a change in the characteristic shape as a function of distance, x, for the differential load. Again, the waveform is generated using the nonlinear function $B(x)=[(F2-F1)/F]/\Delta load$ as a function of distance obtained from the phase locker 38. As can be seen, the unloaded waveform is relatively flat. In contrast, the loaded waveform oscillates. The multiple slope changes over a short distance of the loaded waveform are caused by the acoustic wave, passing between the transmitter transducer and the receiver transducer in one or both Sensors S1 and S2, being altered by a crack closure or opening. This waveform may be compared to the crack closure or opening data of FIG. 6B by the analysis engine 34 to see if both events are occurring. FIG. 6B is a measure of the amplitude of the acoustic wave as a function of position, x, while FIG. 6D is a measure of the phase-locking phase-related parameter $B(x)$ as a function of position. If both windows indicate active complex asperity behavior from closing/opening points of contact and localized crack plasticity, the shape of the $B(x)$ is consistent with crack dynamics. Since the data for FIGS. 6B and 6D come from two, independent, time-related measurements, they provide clear indicators of crack activity measured with two different time events: one at acoustic wave propagation speed and the other at, for example, train speed.

For one or more of the windows shown in FIGS. 6A–6D, the analysis engine 34 compares the waveform data to pre-stored waveform pattern data in the data archive 22 to determine the significance and/or severity of the characteristic, e.g., defect, in the material. The four windows are derived from acoustic data. FIG. 6A is obtained directly from backscattered amplitudes from S1 or S2. FIG. 6B is obtained from transmitted wave amplitude for unloaded vs. loaded conditions. FIG. 6C is a measure of a nonlinearity parameter, B(x), as a function of position along the sample. FIG. 6D is a measure of the same B(x) parameter sorted out because it exhibits complex behavior such as asperity variations as a function of position indicative of crack dynamics.

Figure 7A:
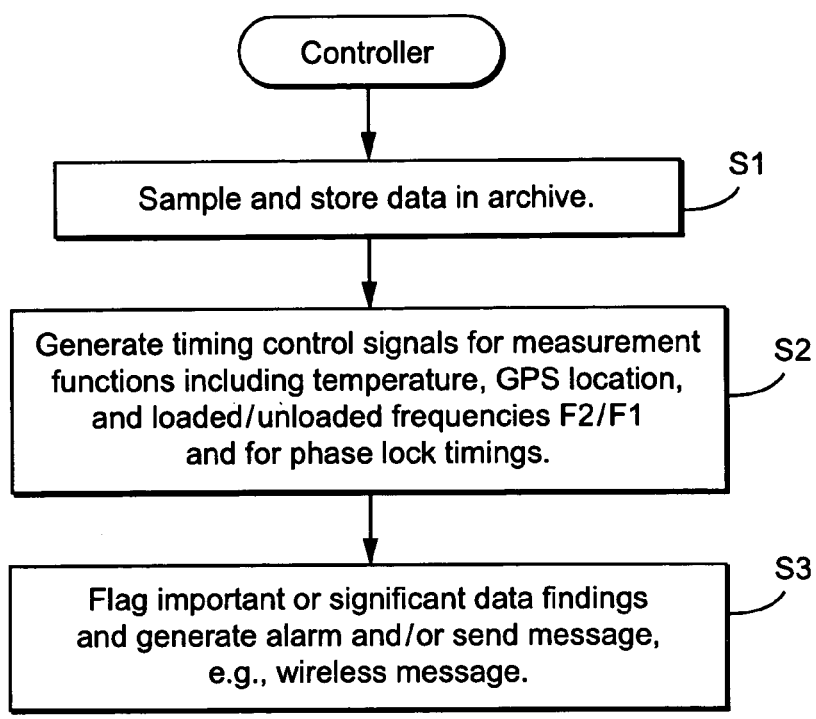
FIG. 7A is a flow chart diagram illustrating example procedures that may be implemented by the controller in FIG. 4.

FIG. 7A illustrates a flow diagram of example procedures that may be performed by controller 30. A first function is to control the sampling and storage of the data used to generate the waveforms in the windows of FIGS. 6A–6D and store them in the data archive 22 (step S1). The controller also generates timing control signals for measurement functions including the thermal sensor 36 temperature measurement, the GPS 42 location measurement (latitude/longitude), loaded and unloaded frequencies F2/F1, and phase lock timings used in phase locker 38 shown in FIG. 5 (step S2). Controller 30 further flags important or significant data findings identified by the analysis engine 34 and generates alarms and/or sends messages, e.g., a message via radio transceiver 44 (step S3). For example, if a severe flaw or dangerous situation is detected in a railway system context, the controller 30 may send an alarm or warning message via radio transceiver 44 to the train driver and to the central train control facility for appropriate remedial action.

Figure 7B:
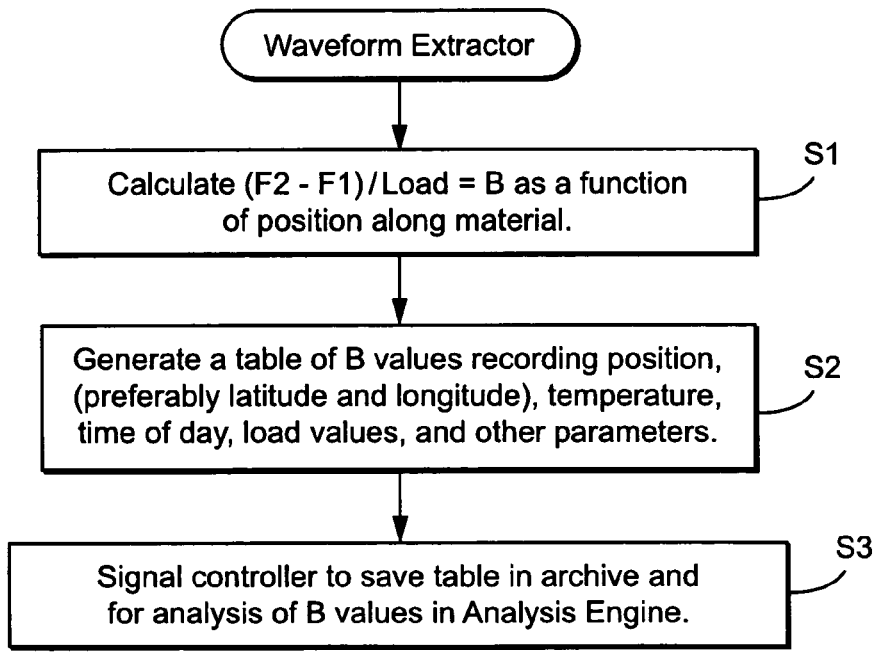
FIG. 7B is a flow chart diagram illustrating example procedures that may be implemented by the waveform extractor shown in FIG. 4.

Example procedures implemented by the waveform extractor 32 are illustrated in the flow chart FIG. 7B. The waveform extractor 32 calculates the nonlinear function B(x) using the formula [(F2–F1)/F]/Δload as a function of position along the material to be tested (step S1). The extractor 32 generates a table of nonlinear B(x) values according to position (preferably latitude and longitude determined from the GPS receiver 42), temperature from the thermal sensor 36, time of day, load values and other parameters (step S2). The waveform extractor 32 signals to the controller 30 to save that table in the data archive 22 and for subsequent analysis of the B(x) values in the analysis engine 34 to generate, for example, one or more of the windows shown in FIGS. 6A–6D (step S3).

Figure 7C:
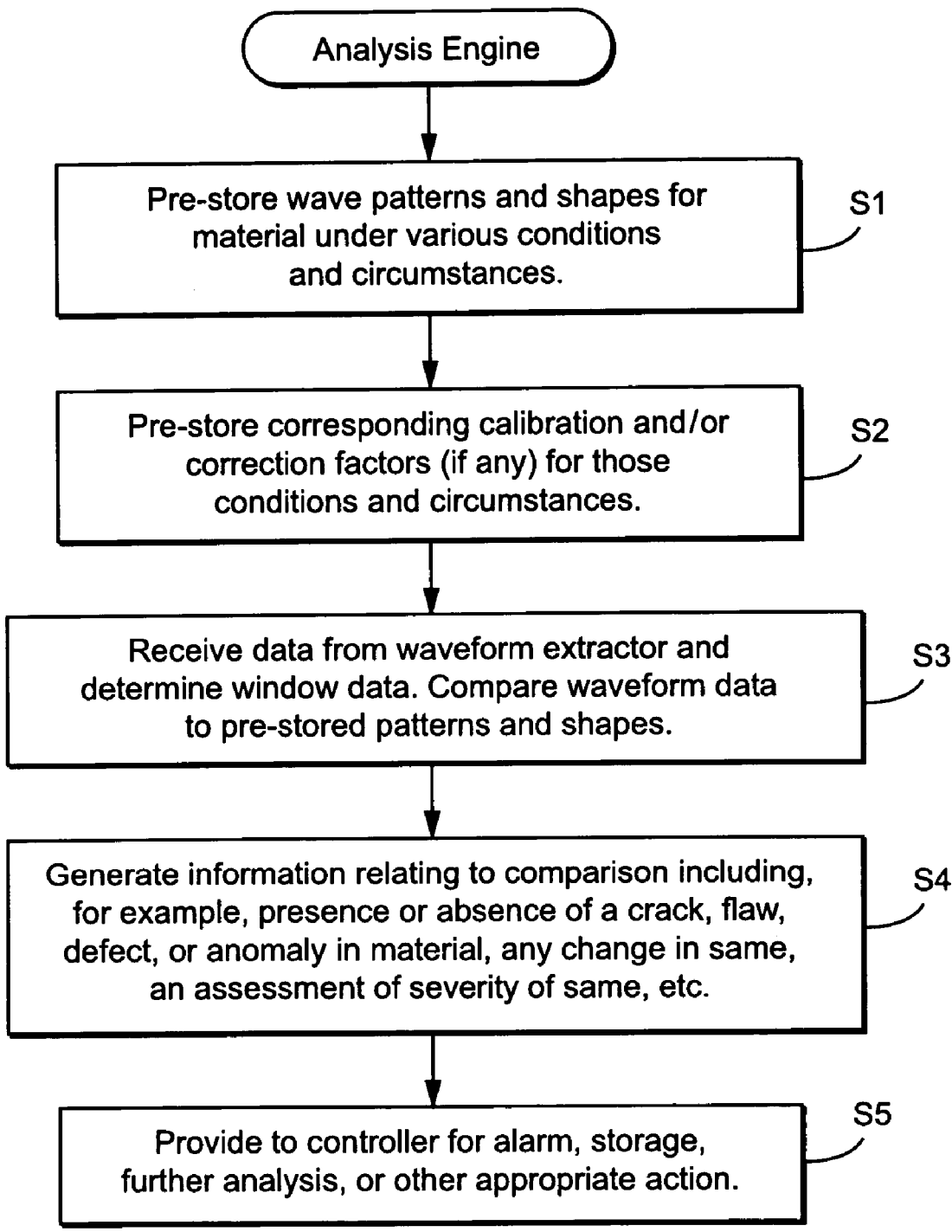
FIG. 7C is a flow chart diagram illustrating example procedures that may be used to implement the analysis engine shown in FIG. 4.

Example procedures that may be performed by the analysis engine 34 are shown in the flowchart of FIG. 7C. The analysis engine 34 pre-stores wave patterns and shapes for material under various conditions and circumstances (step S1). In addition, the corresponding calibration and/or correction factors (if any), e.g., for temperature-induced stress, are pre-stored for those conditions and circumstances employed in step S1 (step S2). The analysis engine 34 receives waveform data from the waveform extractor 32 and determines data used to generate one or more of the windows shown in FIGS. 6A–6D. The analysis engine 34 compares the waveform data to pre-stored patterns and shapes stored, for example, in the data archive 22 (step S3). The analysis engine 34 generates information relating to the comparison including, for example, the presence or absence of a crack, flaw, defect or anomaly in the material, any change in the material or in the crack flaw defect or anomaly, microstructure variation, chemistry variation, and the assessment of the severity of any of these (step S4). The analysis engine 34 uses stored wave-forms and maximum/minimum normalized deviation parameters from those stored wave-forms to classify the measurement data. If the data is out of range, it is flagged as suspicious requiring further inspection and/or testing. The analysis engine 34 provides such information to the controller 30 for an alarm, storage, further analysis, and/or other appropriate action (Step S5).

Figure 8B:
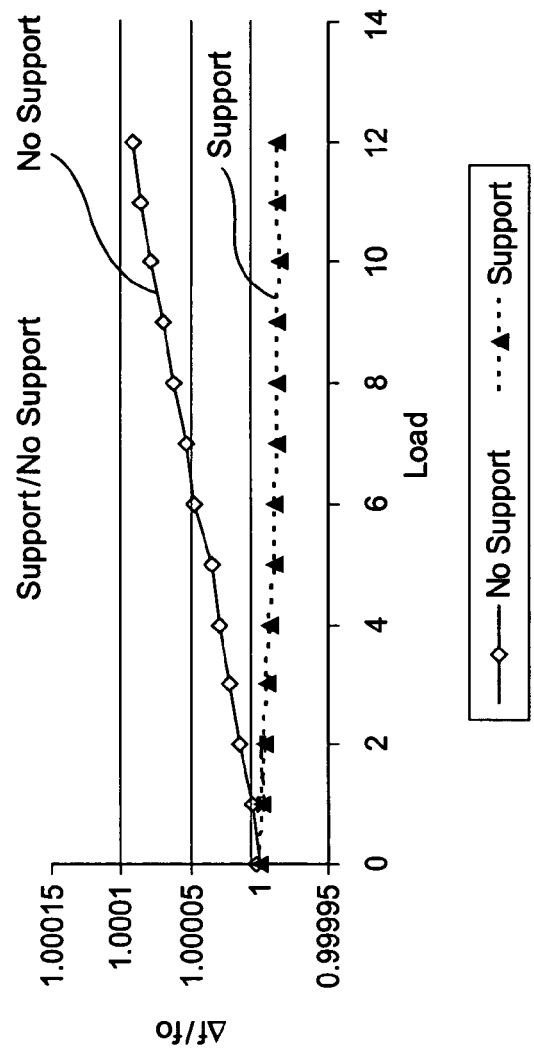
FIG. 8B graphs normalized frequency change of the supported and unsupported rail from FIG. 8A with respect to load on the rail.
Figure 8A:
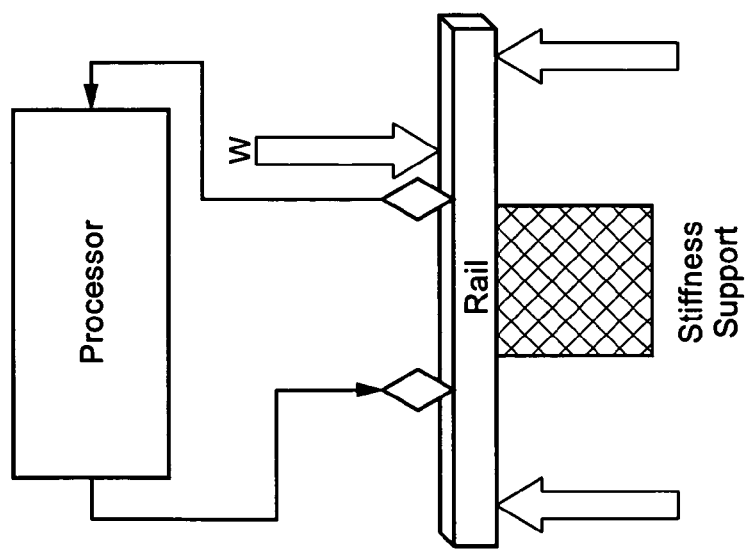
FIG. 8A shows a supported rail test piece.

Several tests were performed to determine the effectiveness of the non-limiting, example application to rail testing and assessment of rail samples. The acoustic waves used in these tests were Sezawa type waves that travel through the rail near its top surface. FIG. 8A shows a rail sample being tested using the phase-locking stiffness assessment described above under two conditions: supported as shown in the FIG. 8A and unsupported. The supported test simulates the portion of a rail directly over a railroad tie, and the unsupported test simulates the portion of a rail between two railroad ties. The graph in FIG. 8B shows change in frequency (F2–F1) or $\Delta f$, normalized as $\Delta f/f_o$, along the vertical axis as the load increases along the horizontal axis. The upper curve shows the change in frequency (F2–F1) or $\Delta f$, normalized as $\Delta f/f_o$, as the load increases for the unsupported rail. The lower curve shows the change in frequency (F2–F1) or $\Delta f$, normalized as $\Delta f/f_o$, as the load increases for the supported rail. The decreasing $\Delta f/f_o$ in the lower curve shows that the supported rail goes under non-bending compression as the load increases. The increasing $\Delta f/f_o$ in the upper curve shows that the supported rail top surface goes under compression as the load increases. Thus, the acoustic wave analysis methodology can discern the difference between a bending, less stiff rail (unsupported) and one that is not bending (more stiff), even though the acoustic wave in these tests traveled near the surface of the rail.

Figure 9B:
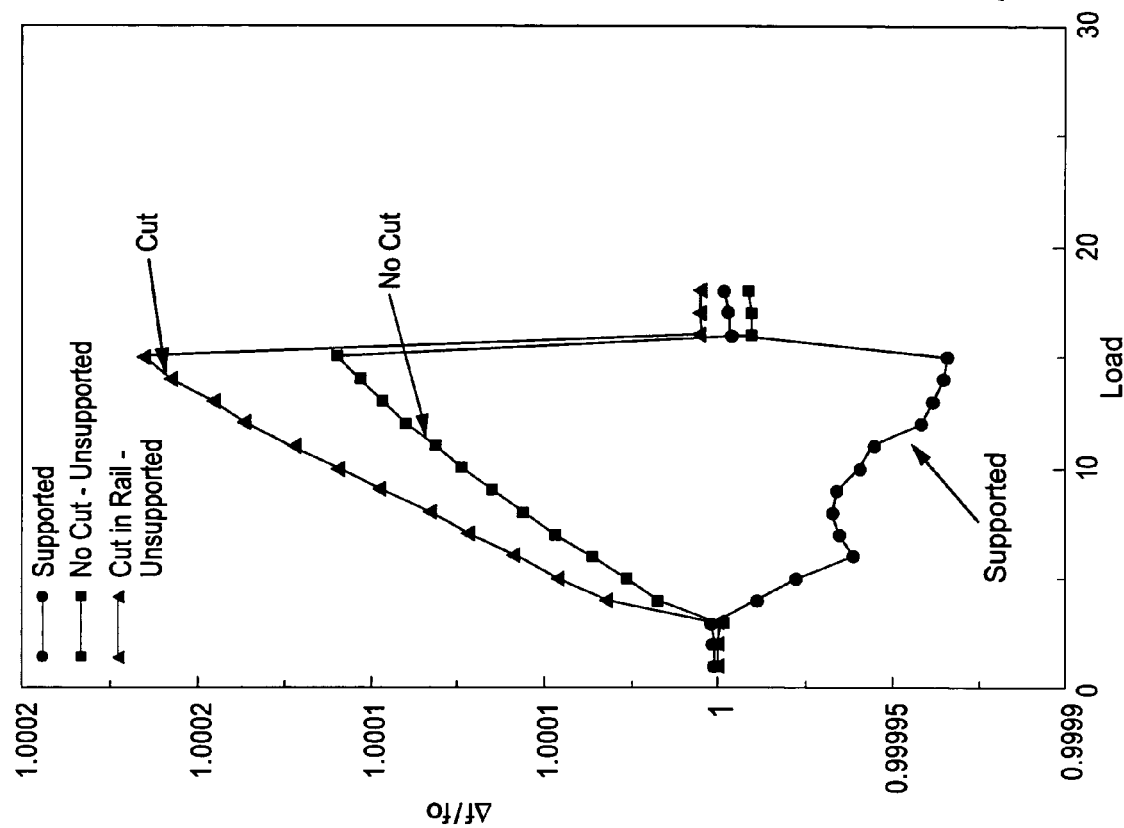
FIG. 9B graphs normalized frequency change of the supported and unsupported rail from FIG. 9A with respect to load on the rail when the rail foot is cut and not cut.
Figure 9A:
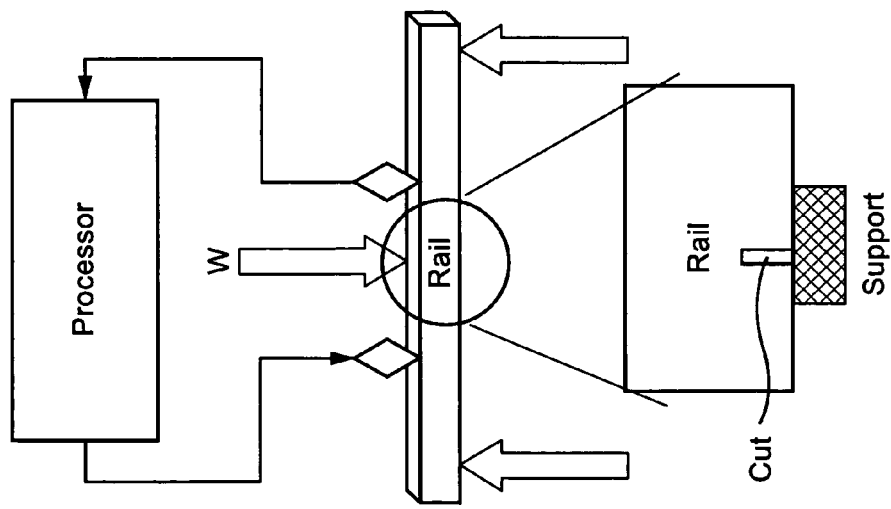
FIG. 9A shows a supported rail test piece with a cut in the foot of the rail directly above the support.

FIG. 9A shows a supported rail sample that includes a cut in the "foot" or bottom of the rail directly above the support. Placing the cut at the rail foot is significant because the Sezawa wave travels along the rail just below the top surface but above the cut and does not reflect or scatter back from the cut. FIG. 9B graphs change in frequency (F2–F1) or $\Delta f$, normalized as $\Delta f/f_o$, along the vertical axis as the load increases along the horizontal axis for the rail without a cut and the rail with a cut. Comparison of the cut and no-cut graphs shows sensitivity to the cut even though it is in the foot of the rail where the acoustic wave is not present. The unsupported rail with no cut behaves normally as it is loaded, going under compression on the top surface. With the cut rail, the top surface experiences even more compression for the same load (the cut graph shows a higher $\Delta f/f_o$ for the same load). When the rail is supported, the $\Delta f/f_o$ curve decreases with load, consistent with the lower graph in FIG. 8B.

FIGS. 10A–10D show four different rail samples graphing amplitude on the vertical axis and time on the horizontal axis. The first rail in FIG. 10A has one crack or flaw. The second rail in FIG. 10B has two cracks or flaws of about the same size. The third rail in FIG. 10C has one crack or flaw smaller than the crack shown in FIG. 10A. The fourth rail in FIG. 10D has two cracks or flaws of different sizes. The graphs in each Figure show the excitation or transmitted acoustic wave/pulse from the transmitter transducer for each sensor S1 and S2, and a reflected (or scattered) acoustic wave/pulse later in time. In the graphs shown in FIGS. 10B and 10D, there are two sets of reflections because the two cracks are detected. The graph in FIG. 10C shows a smaller amplitude reflections (compared to FIG. 10A) because the crack is smaller in size. The graph in FIG. 10D shows larger amplitude reflections for the larger crack and smaller amplitude reflections for the smaller crack.

Figure 11B:
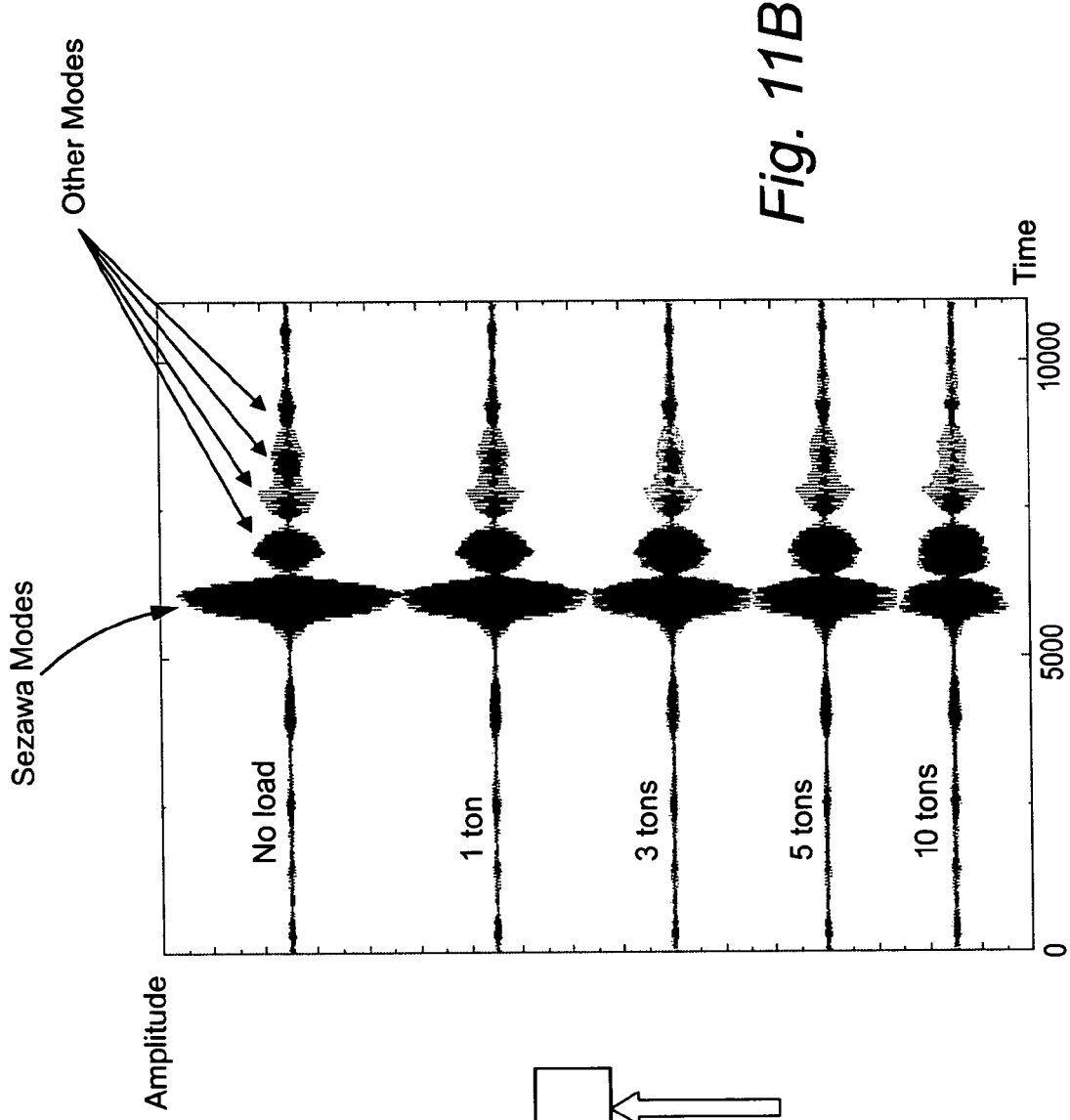
FIG. 11B shows a series of waveforms that reveal crack closing with increasing load.
Figure 11A:
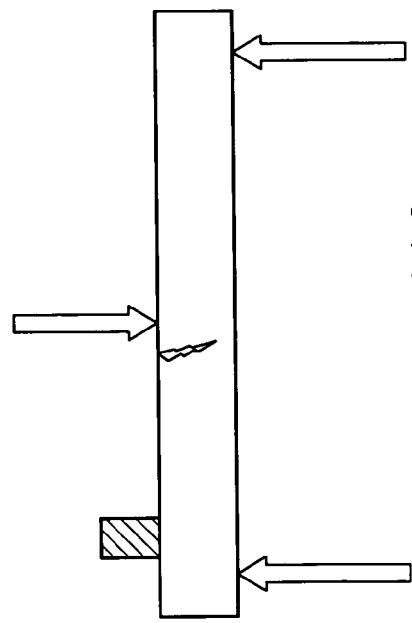
FIG. 11A shows a supported rail test piece.

FIG. 11A shows a rail sample with a subsurface crack. FIG. 11B shows five amplitude v. time graphs of acoustic energy reflected from the crack. Each graph shows a different increasing load. As the load increases, the crack closes, and the reflected signal amplitude decreases because more acoustic energy passes through the closing/narrower crack. If the load were reduced, the crack would open, and the reflected acoustic energy amplitude would increase. This crack closure detection is valuable because in addition to detecting rail strain and changes in rail strain, the dynamics of a rail flaw can be assessed.

The present invention provides a superior inspection and assessment method and apparatus that may be applied to test and assess any material. One non-limiting advantageous example is to railway inspection. The invention permits detecting and assessing the effects of defects and flaws on material performance. The four measurement windows described in FIG. 6A-6C permit multiple different characteristics of the material, including, for example, the material stiffness as shown in FIG. 6C to be determined from a moving vehicle. This new capability enables higher speed testing as well as robust material assessments. Additional benefits include:

- effective measurement without contacting the material and unaffected by dirt, grease, corrosion, and blind spots.
- dynamic differential measurement of load versus no load rail strain.
- direct measurement of transverse head defects through scattering.
- detection of rail foot defects based on detection of stiffness/strain changes in the rail.
- detection of crack closure and opening as an defective assessment tool.
- detect changes in rail residual stress using B(x) and by data archiving from previous inspections.
- integration with GPS location systems permits generation of a rail integrity data base to flag repairs only when necessary.
- detect railbed stiffness problems from rail deformation behavior.

Another non-limiting, example application relates to assessing vehicle roadbed or airplane runway stability. This embodiment uses a first acoustic sensor S1 at a first unloaded (or lightly loaded) wheel of a vehicle performing testing to transmit an acoustic wave in the roadbed/runway and detects that transmitted wave some distance from the transmitter in S1. The wave is detected by a sensor in S1 and used in a phase-locked system to measure a frequency F1. A second sensor S2 is located at a second wheel supporting a heavier load than the first wheel and determines in a similar fashion frequency F2. The stiffness of the roadbed/runway is then calculated based on the differential measurements from S1 and S2. Loss of foundation under the roadbed/runway is detected by the measured changes.

Another non-limiting, example application relates to determining the weight of moving vehicles over a road or other surface. Only one sensor system S1 is needed mounted in the roadbed. It measures the unloaded roadbed using an acoustic wave propagating in the roadbed material. As a vehicle passes over the sensor acoustic path, the roadbed deforms (strains) caused by the weight of the vehicle. The differential measurement is achieved by looking at the unloaded frequency F1 and the loaded frequency F2 to calculate the vehicle weight.

Another non-limiting, example application measures the load path on a structure. Sensor S1 and S2 measure different acoustic propagation paths on a structure to determine unloaded frequencies F1 and F2. The structure is loaded and the frequencies F1' and F2' are measured and compared to the unloaded case to determine the affect of the applied load. This data is stored and archived. At some future time the measurement is repeated. The repeated measurement is used to assess if the structure has changed over time as to distribution of load. The application provides an assessment of the stability of the complex internal structure from a few simple measurements. An array of sensor systems, S1, can be used to determine a matrix of complex loads with this concept.

Another non-limiting, example application relates to a ground-water flow device that is based on a transducer pair in a sensor S1 that generates a frequency F1 for a given subterranean hydrological pressure condition. The hydraulic pressure drives water to flow through the soil. The transmitter transducer in sensor S1 propagates an acoustic wave through the soil to the receiver transducer. The system establishes F1 accurately over a period of time. The system then changes the role of the transmitter and receiver transducers, reversing the acoustic wave propagation direction and creating a new frequency F2. The change in frequency is related to the water flow through the soil caused by hydraulic pressure. By placing sensors at different depths and in different planes, a vector flow profile can be determined by selecting the transducer pairs for appropriate combinations of sensors in the coordinate directions.

While practical and preferred implementations of example embodiments and applications have been described, it is to be understood that the invention is not limited to any disclosed embodiment, implementation, or application and on the contrary, is intended to cover various modifications and equivalent arrangements included within the scope of the appended claims.

The invention claimed is:

1. A method for assessing a characteristic of a material, comprising:
   (a) propagating an acoustic wave through the material in an unloaded condition;
   (b) detecting a reflection or a transmission of the acoustic wave;
   (c) determining a parameter of the transmitted acoustic wave or the reflected acoustic wave using first and second sensors mounted on a movable load and separated by a known length;
   (d) repeating steps (a)–(c) with the material in a loaded condition;
   (e) determining a parameter difference between the unloaded and loaded conditions; and
   (f) determining from the parameter difference the characteristic of the material.

2. The method in claim 1, wherein the parameter is related to a velocity of the transmitted acoustic wave or the reflected acoustic wave and the characteristic is a strain, stress, density or a stiffness of the material.

3. The method in claim 1, wherein the characteristic is a crack, defect, anomaly, microstructure variation, chemistry variation, or flaw in the material.

4. The method in claim 3, further comprising:
determining a change in the crack, defect, anomaly, microstructure variation, chemistry variation, or flaw in the material based on the parameter difference.

5. The method in claim 3, further comprising:
repeating steps (a)–(f) for different positions along the material and generating therefrom data corresponding to one or more waveforms representing the characteristic of the material with respect to position, and
assessing an effect of the crack, defect, anomaly, microstructure variation, chemistry variation, or flaw in the material based on a detected nonlinearity in the data corresponding to one or more waveforms.

6. The method in claim 5, wherein the data corresponding to one or more waveforms is used to determine one or more of the following relationships: a strain, stress,
density or stiffness relationship for the unloaded material and the loaded material, a crack, defect, anomaly, microstructure variation, chemistry variation, or flaw detection relationship, and data corresponding to a waveform that shows an effect of the crack, defect, anomaly, microstructure variation, chemistry variation, or flaw on the material.

7. The method in claim 6, further comprising:
determining an amplitude of the transmitted acoustic wave or the reflected acoustic wave for different positions along the material with the material in an unloaded condition;
determining an amplitude of the transmitted acoustic wave or the reflected acoustic wave for different positions along the material with the material in a loaded condition; and
generating data corresponding to one or more waveforms representing the characteristic of the material with respect to position based on the determined amplitudes.

8. The method in claim 3, further comprising:
determining an amplitude of the transmitted acoustic wave or the reflected acoustic wave for different positions along the material with the material; and
generating data corresponding to one or more waveforms representing the characteristic of the material with respect to position based on the determined amplitudes.

9. The method in claim 8, further comprising:
detecting the crack, defect, anomaly, microstructure variation, chemistry variation, or flaw on the material using the one or more waveforms.

10. The method in claim 1, wherein the material is any material through which an acoustic wave can propagate.

11. The method in claim 1, further comprising:
detecting a parameter in an environment of the material and factoring that detected parameter into the material characteristic determination.

12. The method in claim 11, wherein the detected parameter is temperature, pressure, humidity electric field, magnetic field or other environmental condition.

13. The method in claim 1, further comprising:
performing steps (a)–(f) plural times to determine a stability of the material.

14. The method in claim 1, wherein the acoustic wave is a guided wave or a higher-order guided wave.

15. The method in claim 1, wherein steps (a)–(f) are performed without contacting the material or by contact to the material.

16. The method in claim 1, further comprising:
moving the movable load over the material to produce both the loaded condition and the unloaded condition.

17. The method in claim 1, wherein the parameter is related to the velocity of the acoustic wave, the method further comprising:
dividing the normalized velocity parameter difference by the load to determine a dividend, and
determining the characteristic based on the dividend.

18. The method in claim 17, wherein the first and second sensors are phase lock loop sensors and the acoustic wave is generated at a first frequency, further comprising:
determining a second frequency of the reflected acoustic wave in an unloaded condition and a third frequency of the reflected acoustic wave in a loaded condition, and
determining a frequency difference between the second and third frequencies,
wherein the velocity difference can be determined from the frequency difference.

19. The method in claim 1, wherein the acoustic wave propagates under a surface layer of the material.

20. The method in claim 1, wherein the acoustic wave is an acoustic surface, guided, shear, compressive, or bulk wave.

21. The method in claim 1, further comprising:
using loaded and unloaded acoustic wave data to determine a dynamic or static crack-opening, a crack-closing, or a changed condition in the material.

22. The method in claim 1, further comprising:
archiving data obtained from any of steps (a)–(f) for monitoring changes in the material over time.

23. The method in claim 1, further comprising:
transmitting data obtained from any of steps (a)–(f) by wireless link.

24. A method for assessing a characteristic of a material, comprising:
(a) propagating an acoustic wave through the material in an unloaded condition;
(b) detecting a reflection or a transmission of the acoustic wave;
(c) determining a parameter of the transmitted acoustic wave or the reflected acoustic wave;
(d) repeating steps (a)–(c) with the material in a loaded condition;
(e) determining a parameter difference between the unloaded and loaded conditions; and
(f) determining from the parameter difference the characteristic of the material, the method further comprising:
repeating steps (a)–(f) for different positions along the material and generating therefrom data corresponding to one or more waveforms representing the characteristic of the material with respect to position, and
assessing an effect of a crack, defect, anomaly, microstructure variation, chemistry variation, or flaw in the material based on a detected nonlinearity in the data corresponding to one or more waveforms,
wherein the parameter is a velocity of the acoustic wave or the reflected acoustic wave determined for different positions along the material, further comprising:
generating data corresponding to one or more waveforms representing the characteristic of the material with respect to position based on the velocity parameter.

25. A method for assessing a characteristic of a material, comprising:
(a) propagating an acoustic wave through the material in an unloaded condition;
(b) detecting a reflection or a transmission of the acoustic wave;

(c) determining a parameter of the transmitted acoustic wave or the reflected acoustic wave;

(d) repeating steps (a)–(c) with the material in a loaded condition;

(e) determining a parameter difference between the unloaded and loaded conditions; and (f) determining from the parameter difference the characteristic of the material, the method further comprising:

using loaded and unloaded acoustic wave data to determine defect stability from acoustic scattering in the material.

26. A method for assessing a characteristic of a material, comprising:

propagating an acoustic wave through the material under different load conditions;

detecting a reflection or a transmission of the acoustic wave under the different load conditions;

processing information related to the detected acoustic wave to detect dynamically or statically crack-opening or closing of a crack in the material, wherein the processing includes determining a velocity parameter of the detected acoustic wave for unloaded and loaded conditions, determining a velocity difference between the unloaded and loaded velocity parameters, and determining a non-linear characteristic of the velocity difference, and the method further comprising:

determining that a crack, defect, anomaly, microstructure variation, chemistry variation, or flaw in the material likely exists based on the non-linear characteristic of the velocity difference.

27. The method in claim 26, further comprising:

generating a waveform related to the detected acoustic wave under the different load conditions, and analyzing that waveform to detect dynamically or statically crack-opening or closing of a crack in the material.

28. The method in claim 26, further comprising:

determining a variation in stress, density or a strain in the material from the processing.

29. The method in claim 26, further comprising:

compensating for an effect of temperature in the processing.

30. The method in claim 26, further comprising:

storing some of the processed information in an archive.

31. The method in claim 26, further comprising:

determining that a crack, defect, anomaly, microstructure variation, chemistry variation, or flaw in the material likely exists based on detecting a reflected acoustic wave whose amplitude exceeds a predetermined value.

32. Apparatus for assessing a characteristic of a material, comprising:

a radiation source for propagating an acoustic wave through the material;

a first transducer for detecting a reflection or a transmission of the acoustic wave at a first position in the material under a first load;

a second transducer for detecting a reflection or a transmission of the acoustic wave at a second position in the material under a second load less than the first load;

electronic circuitry configured to determine (1) a parameter of the transmitted acoustic wave or the reflected acoustic wave for the first and second load conditions, (2) a parameter difference between the first and second load conditions, and (3) from the parameter difference, the characteristic of the material, wherein the first and second transducers are mounted on a movable load and are separated by a predetermined length.

33. The apparatus in claim 32, wherein the parameter is related to a velocity of the transmitted acoustic wave or the reflected acoustic wave and the characteristic is a strain, stress, density or a stiffness of the material.

34. The apparatus in claim 32, wherein the characteristic is a crack, defect, anomaly, microstructure variation, chemistry variation, or flaw in the material.

35. The apparatus in claim 34, the electronic circuitry further configured to determine a change in the crack, defect, anomaly, microstructure variation, chemistry variation, or flaw in the material based on the parameter difference.

36. The apparatus in claim 34, wherein the electronic circuitry further configured to:

repeat (1)–(3) for different positions along the material and generating therefrom one or more waveforms representing the characteristic of the material with respect to position, and assess an effect of the crack, defect, anomaly, microstructure variation, chemistry variation, or flaw in the material based on a detected nonlinearity in the one or more waveforms.

37. The apparatus in claim 36, wherein the electronic circuitry is configured to use the one or more waveforms to generate one or more of the following: a strain, stress, density or stiffness versus position relationship for the unloaded material and the loaded material, a crack, defect, anomaly, microstructure variation, chemistry variation, or flaw detection versus position relationship, and a waveform that shows an effect of the crack, defect, anomaly, microstructure variation, chemistry variation, or flaw on the material.

38. The apparatus in claim 37, wherein the electronic circuitry is configured to:

determine an amplitude of the transmitted acoustic wave or the reflected acoustic wave for different positions along the material with the material in an unloaded condition;

determine an amplitude of the transmitted acoustic wave or the reflected acoustic wave for different positions along the material with the material in a loaded condition; and generate data corresponding to one or more waveforms representing the characteristic of the material with respect to position based on the determined amplitude.

39. The apparatus in claim 38, wherein the parameter is a velocity of the acoustic wave determined for different positions along the material, wherein the electronic circuitry is configured to:

generate data corresponding to one or more waveforms representing the characteristic of the material with respect to position based on the measured velocity parameter.

40. The apparatus in claim 34, wherein the electronic circuitry is configured to:

determine an amplitude of the transmitted acoustic wave or the reflected acoustic wave for different positions along the material with the material; and generate data corresponding to one or more waveforms representing the characteristic of the material with respect to position based on the measured amplitudes.

41. The apparatus in claim 40, wherein the electronic circuitry is configured to:

detect the crack, defect, anomaly, microstructure variation, chemistry variation, or flaw on the material using data corresponding to the one or more waveforms.

42. The apparatus in claim 32, wherein the material is any material through which an acoustic wave can propagate.

43. The apparatus in claim 32, further comprising:
a detector for detecting a parameter in an environment of the material,
wherein the electronic circuitry is configured to factor the detected parameter into the material characteristic determination.

44. The apparatus in claim 43, wherein the detected parameter is temperature, pressure, humidity, electric field, magnetic field.

45. The apparatus in claim 32, wherein the electronic circuitry is configured to perform (1)–(3) plural times to determine a stability of the material.

46. The apparatus in claim 32, wherein the acoustic wave is a guided wave or a higher-order guided wave.

47. The apparatus in claim 32, wherein the first and second transducers do not contact the material.

48. The apparatus in claim 32, wherein the first and second transducers contact the material.

49. The apparatus in claim 32, wherein the movable load is configured to move over a railway track.

50. The apparatus in claim 49, wherein the material is a rail of the railway track, and wherein moving the movable load over the railway track produces the first and second load conditions.

51. The apparatus in claim 50, wherein the electronic circuitry is configured to use acoustic wave data under the first and second load conditions to determine a dynamically or statically crack-opening, a crack-closing, or a changed condition in the rail.

52. The apparatus in claim 50, wherein the electronic circuitry is configured to use acoustic wave data under the first and second load conditions to determine defect stability based on acoustic scattering in the material.

53. The apparatus in claim 50, wherein the parameter is related to the velocity of the acoustic wave, and wherein the electronic circuitry is configured to:
divide the normalized velocity parameter difference by the load to determine a dividend, and
determine the characteristic based on the dividend.

54. The apparatus in claim 53, wherein the first and second sensors are phase lock loop sensors and the acoustic wave is generated at a first frequency, and wherein the electronic circuitry is configured to:
determine a second frequency of the transmitted acoustic wave in the first load condition and a third frequency of the transmitted acoustic wave in the second load condition, and
determine a frequency difference between the second and third frequencies,
wherein the normalized velocity difference can be determined from the normalized frequency difference.

55. The apparatus in claim 32, wherein the acoustic wave propagates under a surface layer of the material.

56. The apparatus in claim 32, wherein the acoustic wave is an acoustic surface, guided, shear, compressive, or bulk wave.

57. The apparatus in claim 32, further comprising:
a transmitter for wirelessly transmitting data obtained from any of (1)–(3).

58. Apparatus for assessing a characteristic of a material, comprising:
a radiation source for propagating an acoustic wave through the material;
a first transducer for detecting a reflection or a transmission of the acoustic wave without contacting the material at a first position under a first load;
a second transducer for detecting a reflection or a transmission of the acoustic wave without contacting the material at a second position under a second load less than the first load;
electronic circuitry configured to determine (1) a parameter of the transmitted acoustic wave or the reflected acoustic wave for the first and second load conditions, (2) a parameter difference between the first and second load conditions, and (3) from the parameter difference, the characteristic of the material;
a memory for archiving data obtained from (1)–(3) for monitoring changes in the material over time; and
a global positioning detector for detecting a global position associated with the (1)–(3),
wherein the electronic circuitry is configured to store associated global position information in the memory.

59. Apparatus for assessing a characteristic of a material, comprising:
a source for propagating an acoustic wave through the material under different load conditions;
a detector for detecting a reflection or a transmission of the acoustic wave under the different load conditions; and
processing circuitry configured to process information related to the detected acoustic wave to detect an opening or closing of a crack in the material.
wherein the processing circuitry is configured to determine a velocity parameter of the detected acoustic wave for less loaded and more loaded conditions, a normalized velocity difference between the less loaded and more loaded velocity parameters, a non-linear characteristic of the velocity difference, and that a crack, defect, anomaly, microstructure variation, chemistry variation, or flaw in the material likely exists based on the non-linear characteristic of the velocity difference.

60. The apparatus in claim 59, further comprising:
generating a waveform related to the detected acoustic wave under the different load conditions, and
analyzing that waveform to detect dynamically or statically an opening or closing of a crack in the material.

61. The apparatus in claim 59, wherein the processing circuitry is configured to determine a stress or a strain in the material.

62. The apparatus in claim 59, wherein the processing circuitry is configured to compensate for an effect of temperature, humidity, pressure, electric field, magnetic field.

63. The apparatus in claim 59, wherein the processing circuitry is configured to storing some of the processed information in an archive.

64. The apparatus in claim 59, wherein the processing circuitry is configured to determine that a flaw in the material likely exists based on detecting a reflected acoustic wave whose amplitude exceeds a predetermined value.

* * * * *